(12) United States Patent
Sitkovsky et al.

(10) Patent No.: US 8,883,500 B2
(45) Date of Patent: Nov. 11, 2014

(54) METHOD OF PREPARING ADENOSINE-RESISTANT ANTI-TUMOR T LYMPHOCYTES FOR ADOPTIVE IMMUNOTHERAPY

(75) Inventors: Michail V. Sitkovsky, Boston, MA (US); Akio Ohta, Newton, MA (US)

(73) Assignee: Northeastern University, Boston, MA (US)

( * ) Notice: Subject to any disclaimer, the term of this patent is extended or adjusted under 35 U.S.C. 154(b) by 120 days.

(21) Appl. No.: 13/133,121

(22) PCT Filed: Dec. 7, 2009

(86) PCT No.: PCT/US2009/067011
§ 371 (c)(1),
(2), (4) Date: Aug. 24, 2011

(87) PCT Pub. No.: WO2010/065959
PCT Pub. Date: Jun. 10, 2010

(65) Prior Publication Data
US 2011/0300183 A1 Dec. 8, 2011

Related U.S. Application Data

(60) Provisional application No. 61/201,010, filed on Dec. 5, 2008, provisional application No. 61/206,607, filed on Feb. 2, 2009.

(51) Int. Cl.
*C12N 5/0783* (2010.01)
*A61K 39/00* (2006.01)
*A61K 35/12* (2006.01)

(52) U.S. Cl.
CPC ........... *A61K 39/011* (2013.01); *C12N 2501/01* (2013.01); *C12N 5/0636* (2013.01); *A61K 2039/5158* (2013.01); *A61K 2035/124* (2013.01)
USPC ....................................................... 435/375

(58) Field of Classification Search
None
See application file for complete search history.

(56) References Cited

U.S. PATENT DOCUMENTS

2006/0093580 A1  5/2006  Iwashima et al.

FOREIGN PATENT DOCUMENTS

WO  WO-02/083152  10/2002
WO  WO 0350241 A2 *  6/2003

OTHER PUBLICATIONS

Tsang et al. (J. Clin. Invest. 118:3619-3628 (2008)).*
Nolan Lab "Troubleshooting and Optimization of Retroviral Transduction Parameters," Oct. 7, 2008 webpage capture, pp. 1-7.*
Erdmann et al. (Blood. 2005; 105: 4707-4714).*
Huang et al., "Role of A2a extracellular adenosine receptor-mediated signalling in adenosine-mediated inhibition of T-cell activation and expansion" Blood, 90(4): 1600-1610 (1997).
Ohta et al., "In vitro induction of T cells that are resistant to A2 adenosine receptor-mediated immunosuppression" British Journal of Pharmacology 156: 297-306 (2009).
Seegmiller, et al., "The effect of adenosine on lymphoid cell proliferation and antibody formation" Ciba Foundation Symposium 48: 249-276 (1977).
Dudley, et al., "Adoptive-Cell-Transfer Therapy for the Treatment of Patients with Cancer", Nat. Rev. Cancer, 3:666-675, Sep. 2003, 11 pages.
Gajewski, et al., "Immune Resistance Orchestrated by the Tumor Microenvironment", Immunol Rev., 213:131-145, 2006, 15 pages.
Gattinoni, et al., "Adoptive Immunotherapy for Cancer: Building on Success", Nat. Rev. Immunol, 6:383-393, May 2006, published online Apr. 18, 2006, 11 pages.
Sevigny, et al., "Activation of Adenosine 2A Receptors Attenuates Allograft Rejection and Alloantigen Recognition", J Immunol., 178:4240-4249, 2007, 11 pages.
Zarek, et al., "$A_{2A}$ Receptor Signaling Promotes Peripheral Tolerance by Inducing T-Cell Anergy and the Generation of Adaptive Regulatory T-Cells", Blood, 111:251-259, 2008, published online Oct. 1, 2007, 10 pages.

* cited by examiner

*Primary Examiner* — Zachary Skelding
(74) *Attorney, Agent, or Firm* — Wilmer Cutler; Pickering Hale and Dorr LLP

(57) ABSTRACT

In the past, adoptive immunotherapy often failed because the transferred immune cells were inactive in vivo. This disclosure provides a method of producing immune cells that are highly active in vivo. The immune cells may be expanded in vitro in the presence of an adenosine receptor agonist or an antisense nucleic acid that downregulates expression of an adenosine receptor, for example. The immune cells may be tumor-infiltrating lymphocytes (TIL), cytotoxic T lymphocytes (CTL), natural killer (NK) cells, or lymphokine-activated killer (LAK) cells, for example. The methods described herein may be used to treat a number of diseases including cancer, infectious diseases, and immunodeficiencies.

38 Claims, 11 Drawing Sheets

METHOD OF PREPARING ADENOSINE-RESISTANT ANTI-TUMOR T LYMPHOCYTES FOR ADOPTIVE IMMUNOTHERAPY

1. RELATED APPLICATIONS

This application is a national stage filing under 35 U.S.C. 371 of International Application No. PCT/US2009/067011, filed on Dec. 5, 2009, which claims the benefit of U.S. Provisional Application Nos. 61/206,607, filed on Feb. 2, 2009 and 61/201,010, filed on Dec. 5, 2008. International Application No. PCT/US2009/067011 designated the U.S. and was published under PCT Article 21 (2) in English.

2. GOVERNMENT SUPPORT

The invention described herein was supported, in whole or in part, by grants R01CA-11256-01, RO1 CA111985-01A2, and AT002788 from the U.S. National Institutes of Health. The U.S. Government has certain rights in the invention.

3. BACKGROUND

Cancer is one of the most serious health concerns in the developed world, and new strategies for fighting cancer are necessary. One promising technique is adoptive immunotherapy, in which immune cells are transplanted into a cancer patient in order to stimulate immune rejection of the cancer cells. One major problem in developing effective adoptive immunotherapy techniques is that sometimes anti-tumor T cells are effective in killing tumor cells in vitro but not inside patients' bodies. The inability of some anti tumor T cells to kill in vivo may be explained by tumor protecting mechanisms. One major tumor projection mechanism is the production of extra-cellular adenosine by the tumor. The adenosine inhibits anti tumor T lymphocytes by signaling via the immunosuppressive A2A and A2B adenosine receptors on the surface of anti tumor lymphocytes. Overcoming this tumor protective mechanism would allow the effective therapeutic use of procedures that can produce significant numbers of anti tumor T cells in vitro. This disclosure addresses an unmet medical need by providing powerful anti-tumor T lymphocytes for adoptive immunotherapy of diseases including cancer, infectious diseases, and immunodeficiencies.

4. SUMMARY

In the past, adoptive immunotherapy for diseases such as cancer and infectious diseases often failed because the transferred immune cells were inactive in vivo. This disclosure provides a method of producing immune cells (e.g., a lymphocyte population) that are highly active in fighting disease in vivo. The immune cells may be cultured and/or expanded in vitro in the presence of an adenosine receptor agonist or an antisense nucleic acid that downregulates expression of an adenosine receptor, for example, an A2A or A2B receptor. In some embodiments, the immune cells comprise a type of cell capable of ADCC (antibody-dependent cell-mediated cytotoxicity), such as natural killer (NK) cells, macrophages, neutrophils, and eosinophils. In some embodiments, the immune cells are obtained from a cancer or tumor; in some embodiments, the immune cells are obtained from the bloodstream. In some embodiments, the immune cells are obtained from a subject suffering from a cancer or tumor, an infectious disease, or an immunodeficiency; in some embodiments, the immune cells are obtained from a subject who is a cell donor and does not suffer from a cancer or tumor, an infectious disease, or an immunodeficiency. In some embodiments, the immune cells comprise lymphoid progenitor-derived cells. In some embodiment, the immune cells comprise lymphocytes. For example, the lymphocytes may be tumor-infiltrating lymphocytes (TIL), cytotoxic T lymphocytes (CTL), natural killer (NK) cells, or lymphokine-activated killer (LAK) cells. In certain embodiments, the cells are genetically modified to recognize and destroy disease-causing cells in a patient, for example, genetically engineering a CTL to express a recombinant T cell receptor specific to a desired antigen. The methods described herein may be used to treat a number of diseases including cancer or tumor, infectious diseases, and immunodeficiencies. The method described herein may also be combined with one or more conventional therapies for the respective diseases. Adoptive therapy with pathogen-recognizing T lymphocytes represents a promising approach where, in certain embodiments, a patient's own anti-pathogen T cells are cultured and/or expanded in vitro such that the T cells are resistant to inhibition in inflamed (or diseased) tissues once they are administered to a patient.

The present disclosure also provides methods for producing anti cancer or tumor cells in vitro that may be transferred in vivo to tumor/cancer-bearing animals in order to destroy the tumors or cancer. This application also describes the stage-dependent use of A2A and A2B receptors agonists that facilitate the negative selection of anti tumor T cells that are resistant to inhibition by the tumor or cancer-protecting mechanism in the tumor or cancer microenvironment.

In one aspect, this application provides a composition comprising an in vitro cultured and/or expanded mammalian lymphocyte population, wherein said lymphocyte population was cultured and/or expanded in the presence of an adenosine receptor agonist. This application also provides a composition comprising an in vitro cultured and/or expanded mammalian immune cell population (e.g., lymphocyte population), wherein said immune cell population was cultured and/or or expanded in the presence of an agonist of an adenosine receptor. In some embodiments, the cell population undergoes in vitro selection in addition to or in place of in vitro expansion. The expansion and/or selection may result in cells that display superior disease-fighting characteristics. In some embodiments, the immune cell population comprises adaptive immune cells (such as T lymphocytes) and/or innate immune cells (such as natural killer cells). In some embodiments, the lymphocyte population comprises TIL, CTL, NK cells, or LAK cells.

The immune cell population may be enriched for cells resistant to adenosine, and/or depleted for cells sensitive to adenosine. In some aspects, the composition further comprises a nucleic acid encoding a recombinant T cell receptor specific to a desired antigen. In some embodiments, the cells express a recombinant T cell receptor specific to a desired antigen.

The adenosine receptor agonist may be selected from an A2A adenosine receptor (A2AR) agonist and an A2B adenosine receptor (A2BR) agonist. In various embodiments, the A2AR agonist is selected from adenosine, APEC, ATL-146e, ATL202, ATL-313, ATL359, ATL844, ATL902, ATL908, ATL1222, ATL9844, binodenoson, CGS21680, CGS 22492C, CHA, CV-3146, CVT-3033, DMPA GW328267X LUF5835, MRE-0094, NECA, regadonoson, or UK-371104. In some embodiments, the A2BR agonist is adenosine, LUF5835, PHPNECA, para substituted 1,3-dialkyl-8-phenylxanthines, 8-[4-[(N-(2-hydroxyethyl)carboxamidomethyl)oxy]phenyl]-1-propylxanthine, BAY 60-6583, or NECA.

In some embodiments, the immune cell population is isolated from a human subject. The subject may suffer from a cancer such as melanoma, prostate cancer, breast cancer, ovarian cancer, esophageal cancer, or kidney cancer. Alternatively, the subject may be a cell donor who does not suffer from cancer. In some aspects, the subject suffers from cancer and has raised an immune response to the cancer. In certain embodiments, the subject suffers from an infectious disease such as a viral infection, a bacterial infection, an intracellular parasite, and an intracellular pathogen. In some aspects, the subject is immuno-deficient.

In certain embodiments, the cultured and/or expanded immune cell population is capable of inhibiting a cancer and/or tumor in vivo. In some aspects, the cultured and/or expanded immune cell population was cultured and/or expanded first in the absence and then in the presence of an adenosine receptor agonist. In some embodiments, the cultured and/or expanded immune cell population was cultured and/or expanded first for about 5 days in the absence of an adenosine receptor agonist, and then for about 2 days in the presence of an adenosine receptor agonist.

The present disclosure also provides a composition comprising an immune cell (e.g., lymphocyte) and an agonist of an adenosine receptor. In some embodiments, the composition further comprises a nucleic acid encoding a recombinant T cell receptor specific to a desired antigen. In some embodiments, the composition further comprises cells expressing a recombinant T cell receptor specific to a desired antigen.

This disclosure further provides a cell culture medium suitable for the expansion and/or selection of immune cells such as lymphocytes, comprising an adenosine receptor agonist. In some aspects, the adenosine receptor agonist is present in an amount sufficient to inhibit the expansion of cells sensitive to adenosine. In some aspects, the adenosine receptor agonist is present in an amount sufficient to inhibit the survival of cells sensitive to adenosine.

Furthermore, this disclosure provides a pharmaceutical preparation comprising the compositions described herein. The pharmaceutical preparation may further comprise a pharmaceutically acceptable carrier, excipient, glidant, lubricant, stabilizer, colorant, or buffer. The pharmaceutical preparation may also comprise an adjuvant. The pharmaceutical preparation may further comprise or be administered in combination with one or more conventional anti-cancer or anti-tumor agent (e.g., a chemotherapy agent), one or more conventional anti-infection agent (e.g., an antibiotic), or one ore more immuno-promoting agent.

In addition, this application provides a use of such a pharmaceutical preparation for the manufacture of a medicament for treating cancer, an infectious disease, or an immunodeficiency in a subject in need thereof.

Among other things, this application discloses a method of making a an immune cell preparation (e.g., a lymphocyte preparation), comprising: (a) collecting an immune cell population from a subject; and (b) culturing and/or expanding said population in vitro in a culture medium in the presence of an agonist of an adenosine receptor.

In some aspects, the methods further comprise a step between steps (a) and (b) of culturing and/or expanding said cell population in the absence of an adenosine receptor agonist. The method may further comprise a step between steps (a) and (b) of culturing and/or expanding said cell population in the absence of an adenosine receptor agonist for about 5 days. The method may further comprise a step of enriching the immune cell population with cells resistant to adenosine. In some embodiments, the method may also comprise a step of removing from the immune cell population cells sensitive to adenosine.

In certain aspects, the agonist of an adenosine receptor is administered to the cell population between about day 5 and about day 7 after collection of the cell population. In some aspects, the agonist is administered starting at day 3, 4, 5, 6, or 7 and ending at day 5, 6, 7, 8, or 9. In some embodiments, the agonist is administered for a period of 1, 2, 3, or 4 or more days. In certain embodiments, the adenosine receptor agonist is absent during a portion of the cell culture period.

The method may further comprise transfecting the immune cells with a recombinant T cell receptor specific to a desired antigen.

The method may further comprise a step of adding an immune cell stimulating ligand such as anti-CD3 and/or anti-CD28 antibody to the cell population. In some embodiments, the cell expansion method involves a stimulation step. The stimulation step may comprise mixing stimulator cells with responder cells (cells to be cultured and/or expanded). The stimulation step may also comprise adding a cell-free stimulation media to the cells to be cultured and/or expanded.

In addition, this application provides an in vitro cultured and/or expanded immune cell (e.g., lymphocyte) population produced by any of the methods herein.

This application still further discloses a method of treating cancer, tumor, infectious disease, or immunodeficiency in a subject in need thereof, comprising administering to said subject an immune cell (e.g., lymphocyte) population, in a therapeutically effective amount, wherein said population was cultured and/or expanded in the presence of an agonist of an adenosine receptor. In some embodiments, the cell population was isolated from the subject in need thereof. Said subject may be a human subject. In various embodiments, the immune cell preparation is administered systemically, intravenously, or locally.

In some embodiments, the method further comprises administering to said subject an additional anti-tumor agent (such as an adenosine receptor antagonist, like caffeine and/or a caffeine derivatives; (−)-(R,S)-mefloquine; 3,7-Dimethyl-1-propargylxanthine; 3-(3-hydroxypropyl)-7-methyl-8-(m-methoxystyryl)-1-propargylxanthine; 3-(3-hydroxypropyl)-8-(3-methoxystyryl)-7-methyl-1-propargylxanthine phosphate disodium salt; 7-methyl-8-styrylxanthine derivatives; 7-(2-phenylethyl)-5-amino-2-(2-furyl)-pyrazolo-[4,3-e]-1,2,4-triazolo[1,5c]pyrimidine; (E)-1,3-diethyl-8-(3,4-dimethoxystyryl)-7-methyl-3,7-dihydro-1H-purine-2,6-dione; aminofuryltriazolo-triazinylaminoethylphenol (ZM 241385); 8-chlorostyrylcaffeine; (E)-1,3-dipropyl-8-(3,4-dimethoxystyryl)-7-methyl-3,7-dihydro-1H-purine-2,6-dione; 2-isopropyl-4-(2-thiazolyl)thieno[3,2-d]pyrimidine-2-amine; the VERNALIS drugs such as VER 6489, VER 6623, VER 6947, VER 7130, VER 7146, VER 7448, VER 7835, VER 8177, VER 11135, VER 6409, VER 6440; pyrazolo[4,3-e]1,2,4-triazolo[1,5-c]pyrimidines; or 5-amino-imidazolo-[4,3-e]-1,2,4-triazolo[1,5-c]pyrimidines.) or anti-tumor therapy. In some embodiments, the additional anti-tumor therapy or agent comprises conjointly administering a chemotherapeutic drug, a therapeutic antibody or portion thereof, surgery, or radiation, or supplemental oxygen (such as greater than 45%, 55%, 65%, 75%, 85%, or 95% oxygen) to the patient. In some embodiments, the methods comprise administering an adjuvant to the patient.

In certain aspects, the infectious disease is selected from a viral infection, a bacterial infection, an intracellular pathogen or intracellular parasite. In some aspects, the methods further comprise administering to said subject an additional anti-infection agent or anti-infection therapy. In some embodiments, the additional agent or therapy is an antibiotic, an antiviral agent, or a therapeutic antibody or portion thereof.

In certain embodiments, the methods herein further comprise administering to said subject an additional immunity-promoting agent or immunity-promoting therapy.

Among other things, the present disclosure provides a composition comprising an in vitro cultured and/or expanded mammalian immune cell population, wherein said population was cultured and/or expanded in the presence of an antisense nucleic acid or nucleic acid analogue that reduces expression of A2A receptor or A2B receptor. This disclosure also provides a composition comprising an in vitro cultured and/or expanded mammalian lymphocyte population, wherein said population was cultured and/or expanded in the presence of an antisense nucleic acid or nucleic acid analogue that reduces expression of A2A receptor or A2B receptor.

This application also provides a method of treating a cancer or tumor in a subject in need thereof, comprising administering to said subject an immune cell (e.g., lymphocyte) population, in a therapeutically effective amount, wherein said population was cultured and/or expanded in the presence of an antisense nucleic acid or nucleic acid analogue that reduces expression of A2A receptor or A2B receptor. In addition, this application provides a method of treating an infectious disease in a subject in need thereof, comprising administering to said subject an immune cell (e.g., lymphocyte) population, in a therapeutically effective amount, wherein said cell population was cultured and/or expanded in the presence of an antisense nucleic acid or nucleic analogue that reduces expression of A2A receptor or A2B receptor. This disclosure further provides a method of treating immune-deficiency a subject in need thereof, comprising administering to said subject an immune cell (e.g., lymphocyte) population, in a therapeutically effective amount, wherein said cell population was cultured and/or expanded in the presence of an antisense nucleic acid or nucleic acid analogue that reduces expression of A2A receptor or A2B receptor.

In some embodiments, the antisense nucleic acid is an siRNA or shRNA. In certain embodiments, the cell population is enriched for cells resistant to adenosine, and/or depleted for cells sensitive to adenosine. In some embodiments, the composition or method further comprises a nucleic acid encoding a recombinant T cell receptor specific to a desired antigen. In various aspects, the cells express a recombinant T cell receptor specific to a desired antigen.

5. BRIEF DESCRIPTION OF THE DRAWINGS

FIG. 1 illustrates an improvement of adoptive immunotherapy by the treatment of anti-tumor T cells with an adenosine receptor agonist. In a first experiment, tumor-bearing mice received adoptive transfer of agonist-untreated anti-tumor effector cells (TDLN) or NECA-treated TDLN (NECA-TDLN) ($1 \times 10^7$ cells). The photograph (left panel) depicts: 1) top row, lungs from untreated mice (control), 2) middle row, lungs from mice that received $1 \times 10^7$ TDLN, and 3) bottom row, lungs from mice that received $1 \times 10^7$ NECA-TDLN. NECA-TDLN significantly improved tumor rejection compared to untreated TDLN (p=0.00045; Student's t-test). Right panel: the graph depicts the number of tumor nodules per lungs in control, TLDN, and TLDN-NECA animals.

FIG. 2 illustrates an improvement of adoptive immunotherapy by the treatment of anti-tumor T cells with an adenosine receptor agonist. In a second experiment, tumor-bearing mice received adoptive transfer of TDLN or NECA-TDLN at $5 \times 10^6$ or $1 \times 10^7$ cells. The picture indicates the lungs from untreated mice (control) and mice that received $5 \times 10^6$ or $1 \times 10^7$ TDLN or NECA-TDLN. NECA-TDLN significantly improved tumor rejection compared to untreated TDLN (p=$2.3 \times 10^{-7}$ for $5 \times 10^6$ cells and p=$3.2 \times 10^{-7}$ for $1 \times 10^7$ cells; Student's t-test). Right panel: the graph depicts the number of tumor nodules per lungs in control, TLDN, and TLDN-NECA animals.

FIG. 5A-5E. Administration of NECA suppressed mixed lymphocyte reaction, but there was significant development of CTL. CTL was induced by mixed lymphocyte culture using spleen cells from C57BL/6 (H-$2^b$) and DBA/2 (H-$2^d$) mice. The cells were cultured for 5 days in the presence or absence of NECA (0.1-10 µM). The resulting cells were examined for their proliferative activity (A), IFN-γ levels in the culture supernatant (B), and cytotoxicity against P815 mastocytoma (C). Effector-target ratio for cytotoxicity assay was 5:1. (D) Proportion of CD4 and CD8 cells after 5 days. Large (activated) cells were gated for the analysis. Data from CTL induced with 10 µM NECA was shown as a representative. There was no marked difference in other concentrations. (E) $CD8^+$ cell expansion during mixed lymphocyte culture. C57BL/6 cells were stimulated after labeling with CFSE and its fluorescence in $CD8^+$ cells was analyzed after 3 days of culture. Large (activated) CD8-expressing cells were gated for the analysis. Numbers in the panels indicate percentage of population. Data shown here represent average±SD of triplicate samples. The statistical significance was calculated by Student's t-test: a, p<0.05; b, p<0.01; c, p<0.001.

Figure 5:
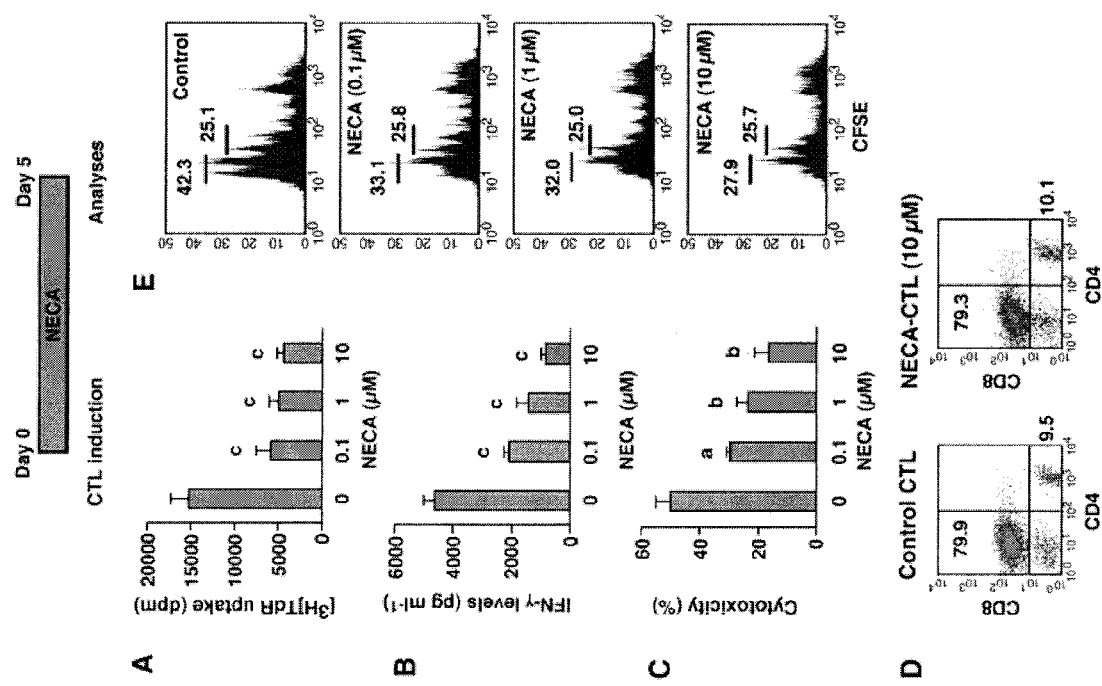
Figure 6:
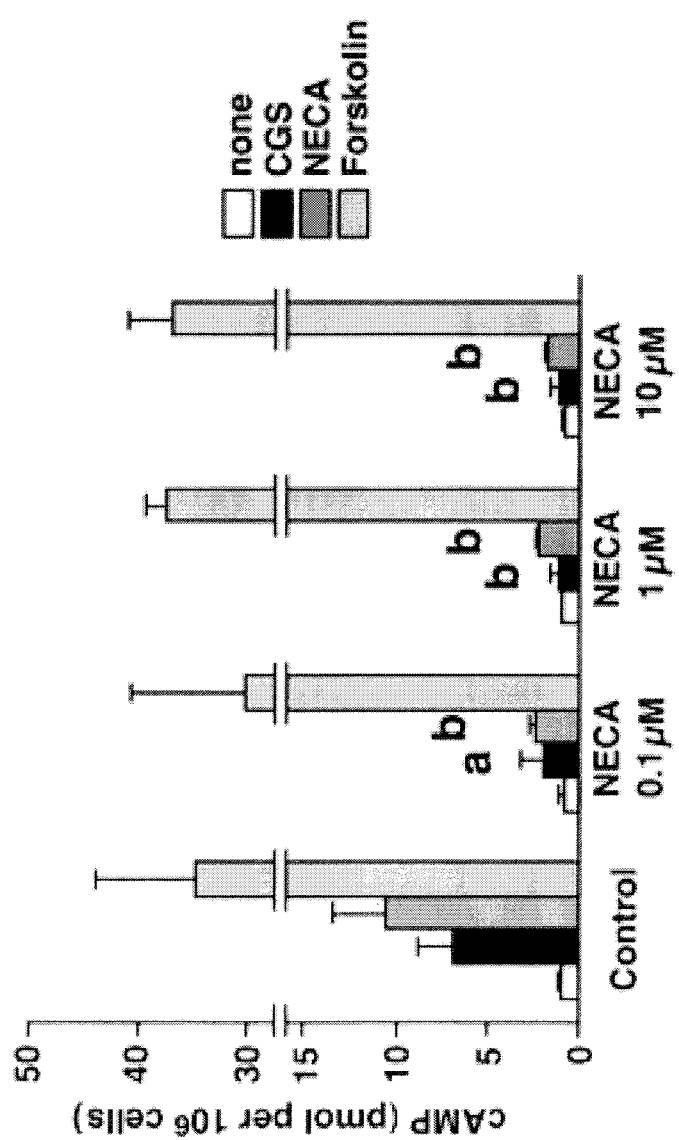

FIG. 6. CTL developed with NECA show impaired response to A2A/A2B adenosine receptor agonists. CTL was induced as described in FIG. 5. cAMP production from the CTL was determined after incubation with A2A/A2B adenosine receptor agonists (CGS and NECA) and adenylate cyclase activator (forskolin). The concentration of cAMP inducers was 10 µM. Data shown here represent average±SD of triplicate samples. The statistical significance was calculated by Student's t-test: a, p<0.05; b, p<0.01 vs control CTL.

Figure 7:
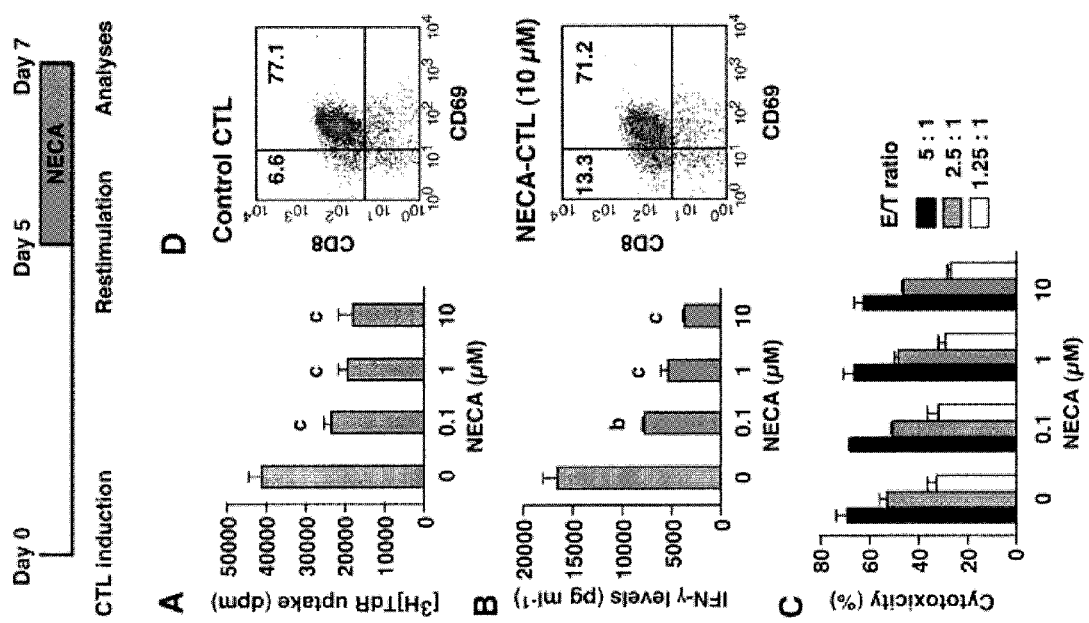

FIG. 7. Cytotoxicity of NECA-CTL was maintained well when NECA was added only during secondary mixed lymphocyte culture. Primary CTL was induced by mixed lymphocyte culture for 5 days. After extensive wash, the cells were restimulated with spleen cells from DBA/2 mice for 2 more days. NECA (0.1-1 µM) was withheld during primary mixed lymphocyte culture and was added for 2 days after restimulation. The resulting cells were examined for their proliferative activity (A), IFN-γ levels in the culture supernatant (B), cytotoxicity against P815 mastocytoma (C), and flowcytometric analysis (D). Effector-target ratio for cytotoxicity assay was 5:1, 2.5:1 and 1.25:1. Data shown here represent average±SD of triplicate samples. The statistical significance was calculated by Student's t-test: b, p<0.01; c, p<0.001.

Figure 8:
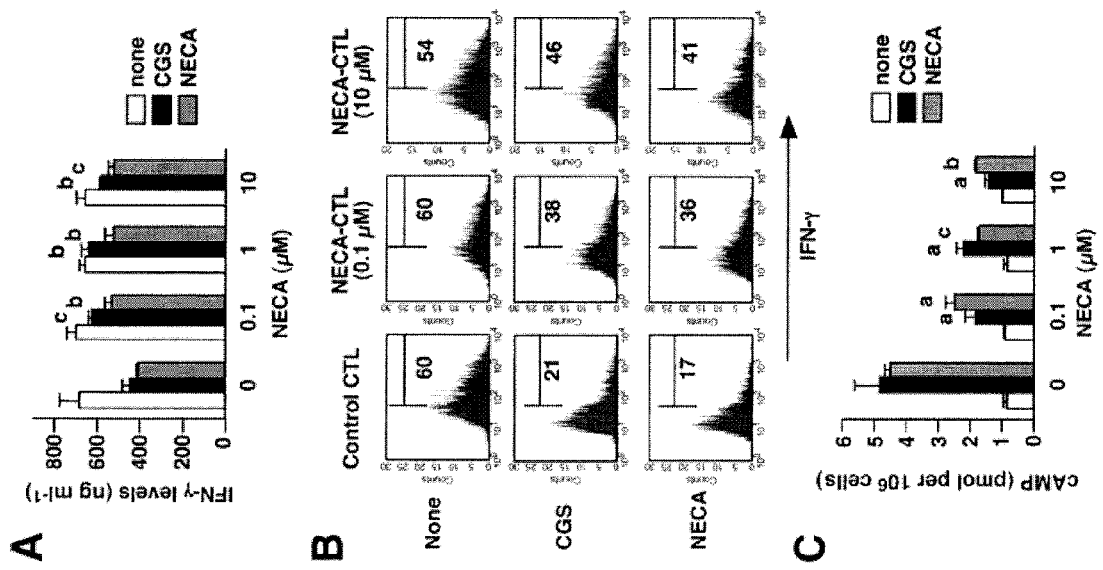

FIG. 8. CTL treated with NECA only for the last 2 days were not only resistant to immunosuppression by A2A/A2B adenosine receptor agonists but also high IFN-γ producers comparable to control CTL. CTL was prepared as in FIG. 7. (A, B) On day 7, the cells were restimulated by immobilized anti-CD3 and anti-CD28 mAbs for 24 h with CGS or NECA (10 µM). (A) IFN-γ levels in the culture supernatant were quantified by ELISA. (B) Intracellular IFN-γ expression in stimulated CTL was evaluated after further incubation with brefeldin A for 2 h. Numbers in each panel show the percentage of IFN-γ producers. The data shown here represent two separate experiments. (C) NECA-CTL treated with NECA only for the last 2 days also show impaired cAMP response to A2A/A2B adenosine receptor agonists. Data shown here represent average±SD of triplicate samples. The statistical significance was calculated by Student's t-test: a, $p<0.05$; b, $p<0.01$; c, $p<0.001$ vs control CTL.

Figure 9:
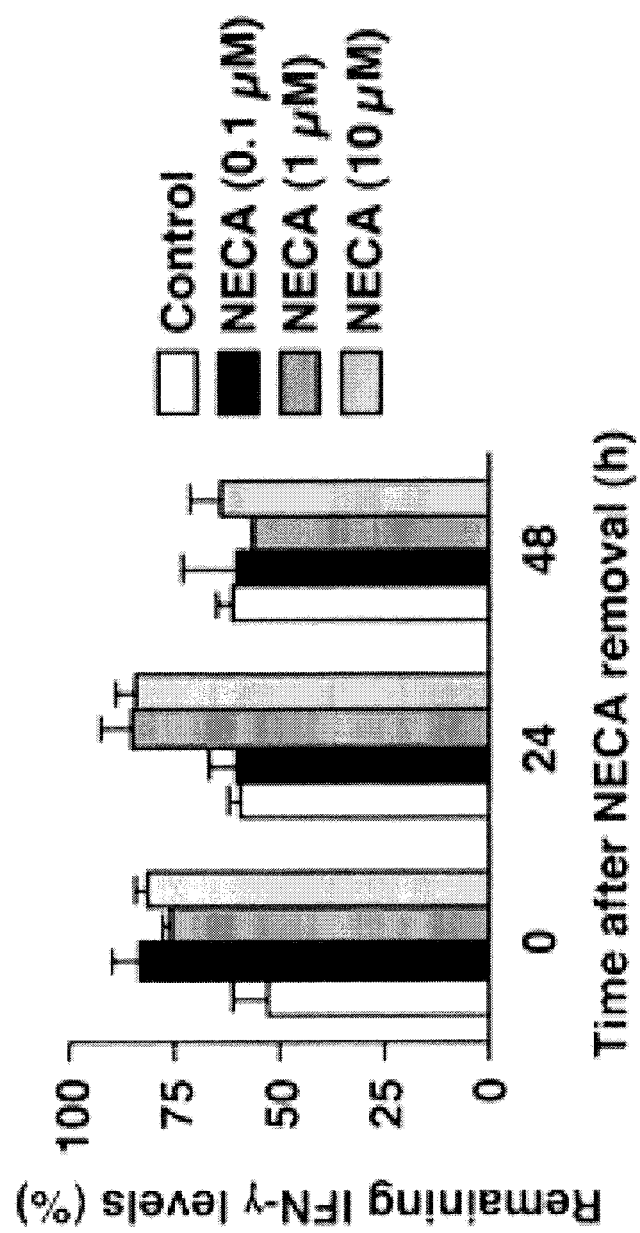

FIG. 9. NECA-CTL maintained their resistance to A2A adenosine receptor stimulation at least for 24 h. NECA was removed by extensive wash 2 days after restimulation. Cells were recultured with IL-2 for 24-48 h, and then IFN-γ production was induced by immobilized anti-CD3 and anti-CD28 mAbs. Inhibitory effect of CGS (10 μM) was expressed as the percentage of remaining IFN-γ levels to control. Data shown here represent average±SD of triplicate samples.

Figure 10:
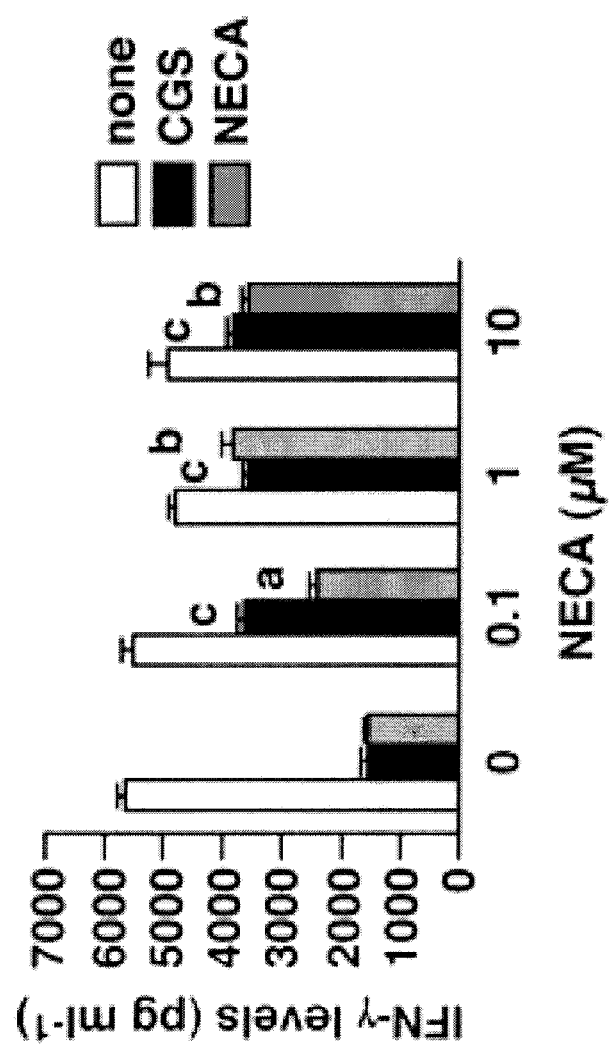

FIG. 10. NECA-CTL could produce high levels of IFN-γ upon recognition of tumor cells even in the presence of A2A/A2B adenosine receptor agonists. CTL was induced as in FIG. 7. In order to activate antigen-specific anti-tumor responses, the same number of CTL were evaluated after co-culture with mitomycin C-treated P815 cells. The susceptibility to A2A/A2B adenosine receptor activation was examined by stimulating in the presence of CGS or NECA (10 μM). IFN-γ levels in the supernatant were determined after 2 days. Data shown here represent average±SD of triplicate samples. The statistical significance was calculated by Student's t-test: a, $p<0.05$; b, $p<0.01$; c, $p<0.001$ vs control CTL.

Figure 11:
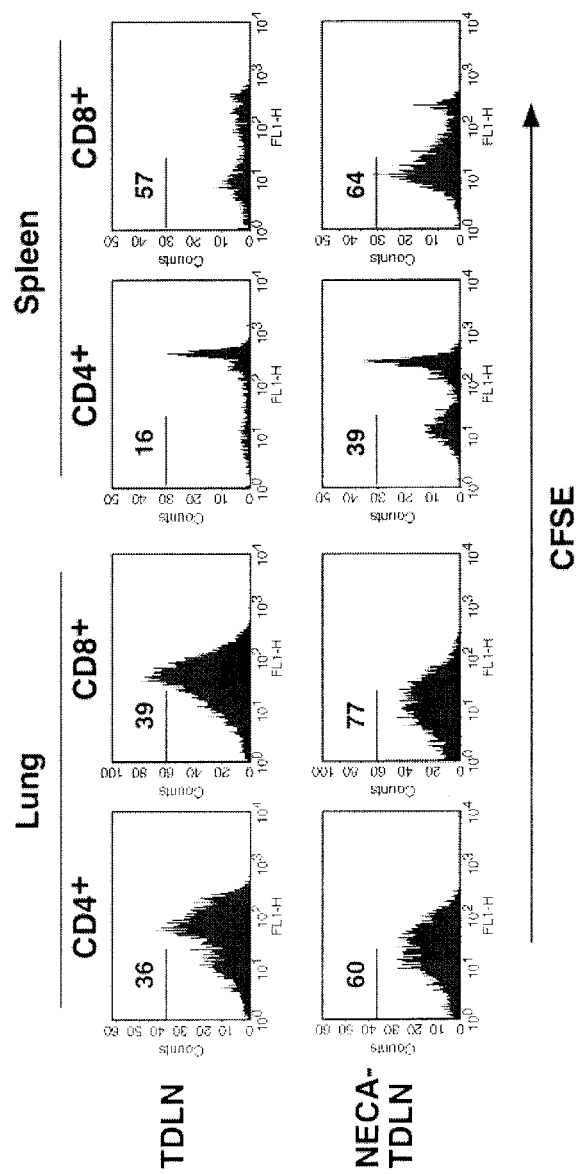

FIG. 11. NECA-pretreated anti-tumor T cells underwent intensive proliferation after adoptive transfer into tumor-bearing mice. Control TDLN and NECA-TDLN were induced from Thy1.1-expressing C57BL/6 mice. After labeling with a fluorescent marker, carboxyfluorescein succinimidyl ester (CFSE), TDLN and NECA-TDLN ($5 \times 10^6$ cells) were transferred into tumor-bearing mice. Diluted fluorescence of CFSE in daughter cells indicates proliferation of the cells. Lymphocytes were isolated from the lung and spleen after 4 days. The data shown here are representative results of CFSE fluorescence in Thy1.1$^+$ cells. The numbers indicate percentage of cells that proliferated for many times. In vivo proliferation of anti-tumor T cells was analyzed in mice received adoptive transfer. NECA-TDLN proliferated better than control TDLN as shown in FIG. 11 suggesting that adenosine-resistant NECA-TDLN could activate well in tumor microenvironment.

6. DETAILED DESCRIPTION

6.1 Definitions

As used herein, "adenosine receptor agonist" or "adenosine receptor activator" are used interchangeably to refer to any agent that promotes signaling of adenosine receptors. An adenosine receptor agonist may mimic or potentiate adenosine signaling, for example. In certain embodiments, the adenosine receptor agonist is a selective adenosine receptor agonist that modulates adenosine receptor signaling 2, 5, 10, 20, 50, 100, 200, 500, or 1000-fold more strongly than signaling of another pathway, such as histamine receptor signaling (such as H3 or H4 histamine receptors), adrenergic receptor signaling (such as β2, β3, or 132 adrenergic receptors), PDE4 signaling, or cholinergic muscarinic receptor signaling. In some embodiments, the agonist is a selective A2A or A2B receptor agonist that modulates adenosine receptor signaling 2, 5, 10, 20, 50, 100, 200, 500, or 1000-fold more strongly than signaling of another pathway, such as adenosine A1 receptor signaling, or adenosine A3 receptor signaling. In certain embodiments, the selective adenosine receptor agonist has a $K_d$ that is less than ½, ⅕, 1/10, 1/20, 1/50, 1/100, 1/200, 1/500, or 1/1000 the $K_d$ of the agonist for another receptor, such as a histamine receptor (such as H3 or H4 histamine receptors), an adrenergic receptor (such as β2, β3, or 132 adrenergic receptors), PDE4, a cholinergic muscarinic receptor, an adenosine A1 receptor, an adenosine A2B receptor, an adenosine A2A receptor, or an adenosine A3 receptor. In some embodiments, the adenosine receptor agonist is a selective A2A receptor agonist. In other embodiments, the adenosine receptor agonist is a selective A2B receptor agonist. In yet other embodiments, the adenosine receptor agonist is an agonist of both A2A and A2B. The adenosine receptor antagonist may also be a small molecule that binds the A2A or A2B receptor. This binding may be covalent or noncovalent. In certain embodiments, the adenosine receptor agonist binds to an adenosine receptor with a $K_d$ of less than 1 μM, 500 nM, 200 nM, 100 nM, 50 nM, 20 nM, 10 nM, 5 nM, 2 nM, or 1 nM. In certain embodiments, the adenosine receptor agonist induces signal transduction pathways characteristic of adenosine binding to that adenosine receptor. For example, the adenosine receptor agonist may induce an increase in cAMP levels relative to a control cell or tissue under similar conditions that is not treated with an adenosine receptor agonist.

An adenosine receptor pathway agonist may promote adenosine receptor pathway signaling by, for example, increasing levels of extracellular adenosine, increasing the number of adenosine receptors per cell, and/or enhancing signaling by an adenosine receptor. An adenosine receptor pathway agonist may act on an adenosine receptor such as an adenosine receptor agonist, upstream of an adenosine receptor, or downstream of an adenosine receptor.

As used herein, "antisense nucleic acid" refers to a nucleic acid that specifically hybridizes (e.g., binds) under cellular conditions, with the target nucleic acid of interest (mRNA and/or genomic DNA) encoding one or more of the target proteins so as to inhibit expression of that protein, e.g., by inhibiting transcription and/or translation, such as by steric hinderance, altering splicing, or inducing cleavage or other enzymatic inactivation of the transcript. The binding may be by conventional base pair complementarity, or, for example, in the case of binding to DNA duplexes, through specific interactions in the major groove of the double helix. Antisense nucleic acids include, without limitation, siRNAs, shRNAs, miRNAs. Antisense nucleic acids may be single stranded, double stranded, or may have one or more single stranded region and one or more double stranded regions.

As used herein, "adjuvant" or "suitable adjuvant" describes a substance capable of enhancing an immune response in a subject. A suitable adjuvant can be, but is not limited to, for example, an immunostimulatory cytokine, SYNTEX adjuvant formulation 1 (SAF-1) composed of 5% (wt/vol) squalene (DASF, Parsippany, N.J.), 2.5 percent Pluronic, L121 polymer (Aldrich Chemical, Milwaukee), and 0.2 percent polysorbate (Tween 80, Sigma) in phosphate-buffered saline. Other suitable adjuvants are well known in the art and include QS-21, Freund's adjuvant (complete and incomplete), alum, aluminum phosphate, aluminum hydroxide, N-acetyl-muramyl-L-threonyl-D-isoglutamine (thr-MDP), N-acetyl-normuramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE) and RIBI, which contains three components extracted from bacteria, monophosphoryl lipid A, trealose dimycolate and cell wall skeleton (MPL+TDM+CWS) in 2% squalene/Tween 80 emulsion. The adjuvant, such as an immunostimulatory cytokine, can be administered before the administration of the immune cells (such as lymphocytes e.g., TIL, CTL, NK cells, or LAK cells), concurrent with the administration of the cells or up to or even greater than five days after the administration of the cells to a subject. QS-21, similarly to alum, complete Freund's adjuvant, SAF, etc., may be administered simultaneously with or within hours of administration of the antigen.

The term "agent" is used herein to denote a chemical compound, a mixture of chemical compounds, a biological macromolecule (such as a nucleic acid, an antibody, a protein or portion thereof, e.g., a peptide), or an extract made from biological materials such as bacteria, plants, fungi, or animal (particularly mammalian) cells or tissues. The activity of such agents may render it suitable as a "therapeutic agent" which is a biologically, physiologically, or pharmacologically active substance (or substances) that acts locally or systemically in a subject.

As used herein, the term "cell donor" refers to an individual that provides immune cells such as lymphocytes (e.g., TIL, CTL, NK cells, or LAK cells) but is not necessarily treated with those cells. In certain embodiments, the cell donor is an individual that is not suffering from a disease for which the immune cells are obtained and further prepared according to the methods described herein. In certain embodiments, the cell donor is an individual that has successfully raised an immune response to a cancer or infectious disease. In certain embodiments, the cell donor is not immunodeficient.

As used herein, the term "enriched" refers to a population having an increased proportion of some desired element relative to a control population. For example, a cell population enriched for cells resistant to adenosine is a cell population that has a greater proportion of cells resistant to adenosine than the starting cell population from which the enriched cell population was derived. In certain embodiments, the enriched cell population is substantially free of a type of cell that normally would "contaminate" or interfere with the function of the desired cell type. It is to be understood that an enriched cell population is not always 100% pure, and may contain cell types other than the cell type of interest.

As used herein, the term "in vitro cultured" refers to cells maintained outside a living organism. While the cells are cultured, they may increase or decrease in number, or may remain at essentially the same number. In some embodiments, one cell subpopulation behaves differently from another cell subpopulation, e.g., one subpopulation expands and another decreases in number. In certain embodiments, the quality of the cells is improved during the in vitro culture phase (e.g., the expanded cells show improved resistance to adenosine and/or are superior at fighting disease), regardless of whether the overall number of cells changes.

As used herein, the term "in vitro expanded" refers to cells multiplied outside a living organism. In certain embodiments, the number of cells increases 2, 5, 10, 20, 50, 100, 200, 500, 1000, 2000, 5000, or 10,000 or more fold in vitro. In some instances, in a heterogeneous population of cells, there is in vitro expansion of one cell subpopulation a simultaneous cell death in another subpopulation, so that the overall number of cells in the heterogeneous population may be constant or even decrease.

As used herein, the term "in vitro selected" refers to cells cultured outside a living organism under conditions that favor the growth or survival of one sub-population of cells relative to another. In some instances, in a heterogeneous population of cells, so that the overall number of cells in the heterogeneous population may be constant, may increase, or may decrease. In certain embodiments, the quality of the cells is improved during the in vitro selection (e.g., the expanded cells show improved resistance to adenosine and/or are superior at fighting disease), regardless of whether the overall number of cells changes.

The term "infectious disease" is well known in the art and refers to a disease caused by one or more pathogens, and may be transmitted (directly or indirectly) from one host to another. An infectious disease may be highly infectious, moderately infectious, or weakly infectious. In certain aspects, the pathogen is a virus, bacterium, fungus, or prion.

"Immune cell stimulating ligands" are well known in the art. Immune cell stimulating ligands can be polypeptides, including antibodies. In some embodiments, the immune cell stimulating ligand activates T cells. Exemplary immune cell stimulating ligands include anti-CD3 antibody, anti-CD28 antibody, anti-Thy-1 antibodies, anti-TAP antibodies, anti-Ly-6 antibodies, anti-CD2 antibodies, and fragments and fusions thereof, and the naturally occurring ligands of CD3, CD28, Thy-1, TAP, Ly-6, and CD2 (as well as functional fragments and fusions thereof). Other immune cell stimulating ligands include interleukins such as IL-2.

The term "immuno-deficient" refers to an organism having deficient immune function compared to a healthy organism. An immuno-deficient organism may have, for example, reduced numbers or activity of one or more of immune cells, lymphocytes, T cells, B cells, TIL, CTL, NK cells, or LAK cells. In certain embodiments, an immuno-deficient subject is infected with human immunodeficiency virus (HIV). In other embodiments, the immuno-deficient subject is receiving immunosuppressive therapy such as, for example, chemotherapy or radiation therapy. In certain embodiments, the immuno-deficient patient suffers from an inherited immunodeficiency such as SCID.

The term "in vitro" as used herein denotes outside a living organism. For instance, cells cultured in a tissue culture vessel are considered in vitro.

The term "lymphocyte" is well-known in the art. As used herein, it encompasses a number of cell types including TIL, CTL, LAK cells, and NK cells.

As used herein, the term "lymphoid progenitor-derived cells" refers to any cell having a precursor that is a lymphoid progenitor cell. The term "lymphoid progenitor-derived cells" therefore encompasses lymphocytes, as well as cells derived from lymphocytes (e.g., cells that lymphocytes differentiate into during the normal course of immune function), and certain cells that are of terminally differentiated and can differentiate into lymphocytes (e.g., lymphoblasts). A lymphoid progenitor cell is a cell type well-known in the art. In some embodiments, "lymphoid progenitor-derived cells" are formed in vivo during natural development and/or immune function. In some embodiments, "lymphoid progenitor-derived cells" are formed in vitro, e.g., when a certain lymphocyte is treated with a molecule that affects its function.

As used herein, a "nucleic acid analogue" refers to a nucleic acid in which at least one nucleoside monomer unit is a "nucleoside analog" and/or at least one phosphate ester internucleotide linkage is a phosphate ester analog. Exemplary classes of nucleic acid analogs are those in which the sugar and internucleotide linkages are replaced with an uncharged, neutral amide, such as a morpholino carbamate and peptide nucleic acids ("PNA") such as those having a N-(2-aminoethyl)glycine amide backbone.

As used herein, "nucleoside analog" refers to a nucleotide in which the nucleobase, the ribose sugar and/or one or more of the phosphate esters is replaced with its respective analog. Exemplary nucleobase and ribose sugar analogs are those previously described in conjunction with nucleoside analogs. Exemplary phosphate ester analogs include, but are not limited to, alkylphosphonates, methylphosphonates, phosphoramidates, phosphotriesters, phosphorothioates, phosphorodithioates, phosphoroselenoates, phosphorodiselenoates, phosphoroanilothioates, phosphoroanilidates, phosphoroamidates, boronophosphates, peptide nucleic acid (PNA) monomers, etc., including any associated counterions, if present.

The phrase "pharmaceutically acceptable carrier" is art-recognized, and includes, for example, pharmaceutically acceptable materials, compositions or vehicles, such as a liquid or solid filler, diluent, solvent or encapsulating material involved in carrying or transporting any subject composition, from one organ, or portion of the body, to another organ, or portion of the body. Each carrier must be "acceptable" in the sense of being compatible with the other ingredients of a subject composition and not injurious to the patient. In certain embodiments, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "reduces expression" i.e. of a gene herein refers to a measurable decrease in the transcript and or protein level corresponding to that gene. In certain embodiments, a transcript or protein level is reduced by to ½, ⅕, 1/10, 1/20, 1/50, 1/100 or less of its original level.

As used herein, a cell "resistant to adenosine" is a cell that shows substantially less adenosine responsiveness than a cell of the same type that has been newly isolated from a normal individual. Adenosine responsiveness may be measured, for example, by an increase in cAMP levels upon stimulation with 1 µM NECA. Adenosine responsiveness may also be measured by a decrease in TCR-triggered gamma interferon secretion. In certain embodiments, a population of cells resistant to adenosine shows no more than a 1.5-fold, 2-fold, 4-fold, 6-fold, or 8-fold increase in cAMP levels upon NECA stimulation. Adenosine resistance may be total or partial; that is, adenosine may inhibit the cell's activity either partially or not at all. However, one of skill in the art will recognize that there are various assays that may be used to measure adenosine resistance or sensitivity.

As used herein, a cell "sensitive to adenosine" is a cell that shows substantially the same adenosine sensitivity as a cell of the same type that has been newly isolated from a normal individual. Adenosine responsiveness may be measured, for example, by an increase in cAMP levels upon stimulation with 1 µM NECA. Adenosine responsiveness may also be measured by a decrease in TCR-triggered gamma interferon secretion. In certain embodiments, a population of cells sensitive to adenosine shows at least a 1.5-fold, 2-fold, 4-fold, 6-fold, or 8-fold increase in cAMP levels upon NECA stimulation. In some embodiments, a cell sensitive to adenosine shows greater than a 6-fold, 8-fold, 10-fold, or 15-fold increase in cAMP treatment upon addition of NECA.

As used herein, "responder cells" refer to immune cells (e.g., lymphocytes) capable of being stimulated by stimulator cells. Responder cells include T-cells, natural killer cells, and T-cell precursors. Responder cells, when stimulated (or when cultured without stimulation), can become T lymphocytes, natural killer cells, and tumor-infiltrating lymphocytes, for example. A responder cell can also be stimulated by an agent other than a cell, such as an MHC molecule complexed with an antigen.

The phrases "systemic administration," "administered systemically," "peripheral administration" and "administered peripherally" are art-recognized, and include the administration of a subject composition, therapeutic or other material at a site remote from the disease being treated. Administration of an agent directly into, onto, or in the vicinity of a lesion of the disease being treated, even if the agent is subsequently distributed systemically, may be termed "local" or "topical" or "regional" administration, other than directly into the central nervous system, e.g., by subcutaneous administration, such that it enters the patient's system and, thus, is subject to metabolism and other like processes. In some embodiments, local administration comprises administration in or near a tumor.

As used herein, the term "small molecule" refers to an organic molecule with a relatively low molecular weight, e.g., less than about 1000 daltons. The term is used to differentiate these organic molecules from typical large biomolecules like nucleic acids, proteins, and complex carbohydrates like heparin and starch.

As used herein, "stimulator cells" refer to cells that have the property of stimulating immune cells (e.g., responder cells). Stimulator cells may be, for example, (MHC)-compatible minor histocompatibility antigen-allogeneic cells, mixed spleen cell cultures, antigen-presenting cells (naturally occurring or non-naturally occurring), macrophages, and/or a cell that recombinantly expresses an MHC molecule. In some embodiments, stimulator cells express antigenic peptides complexed with a desired MHC molecule. In some embodiments, the stimulator cells are tumor cells from a patient to be treated, or cells expressing one or more of the same antigen cells as the patient's tumor cells. One alternative to a stimulator cell is a stimulator that is not a cell. Stimulators that are not cells include: artificial particles that comprising a desired antigen, a MHC molecule complexed to a desired antigen, antibodies such as monoclonal antibodies, cytokines, or a combination of these factors such as a mixture of a monoclonal antibody with a cytokine. In some embodiments, the stimulator is soluble and in other embodiments it is affixed to a matrix. For example, a monoclonal antibody may be immobilized on a matrix.

As used herein, a "subject" or an "individual" refer to a mammal in need of treatment with a composition described herein or a mammal capable of donating cells in order to perform the treatments herein. In certain embodiments, the subject or individual suffers from cancer, immunodeficiency, or an infectious disease. In certain embodiments, the subject or individual does not suffer from a disease. In certain embodiments, the subject or individual is a human. Alternatively, the subject or individual may be a non-human animal. Non-human animals include farm animals (e.g., cows, horses, pigs, sheep, goats) and companion animals (e.g., dogs, cats).

The phrase "therapeutically effective amount" is an art-recognized term. In certain embodiments, the term refers to an amount of a salt or composition disclosed herein that produces some desired effect at a reasonable benefit/risk ratio applicable to any medical treatment. In certain embodiments, the term refers to that amount necessary or sufficient to eliminate or reduce medical symptoms for a period of time. The effective amount may vary depending on such factors as the disease or condition being treated, the particular targeted constructs being administered, the size of the subject, or the severity of the disease or condition. One of ordinary skill in the art may empirically determine the effective amount of a particular composition without necessitating undue experimentation.

The terms "preventing" is art-recognized, and when used in relation to a condition, such as an infectious disease or any other medical condition, is well understood in the art, and includes administration of a composition which reduces the frequency of, or delays the onset of, symptoms of a medical condition in a subject relative to a subject which does not receive the composition. "Preventing" includes prophylactic measures against a disease, disorder or condition from occurring in a mammal which may be predisposed to the disease, disorder and/or condition but has not yet been diagnosed as having it.

The term "treating" is art-recognized and includes inhibiting the disease, disorder or condition, e.g., impeding its progress; and relieving the disease, disorder, or condition, e.g., causing regression of the disease, disorder and/or condition. Treating the disease or condition includes ameliorating at least one symptom of the particular disease or condition, even if the underlying pathophysiology is not affected, such as treating the pain of a subject by administration of an analgesic agent even though such agent does not treat the cause of the pain. The term "treating", "treat" or "treatment" as used herein includes curative, adjunct and palliative treatment.

6.2 Lymphocytes

Various immune cells may be used in adoptive immunotherapy. Immune cells, such as lymphocytes, may be used. In some embodiments, the immune cells comprise adaptive immune cells. In some embodiments, the immune cells comprise innate immune cells (such as natural killer cells or macrophages or neutrophils).

Lymphocytes are well known in the art and include T-lymphocytes, which carry T-cell receptors, B-lymphocytes, which produce antibodies, TIL, CTL, NK cells, and LAK cells. Any one lymphocyte produces one type of TCR or antibody. Each TCR or antibody has specificity for one particular epitope, or antigen binding site, on its cognate antigen. Specific TCRs or antibodies are encoded by genes that are formed from the rearrangement of DNA in a lymphocyte stem cell that encodes the constant ("C"), joining ("J"), variable ("V") regions, and possibly diversity ("D") regions of the TCR or antibody. Mammals typically possess one-hundred thousand to one-hundred million lymphocytes of different specificities. Upon stimulation of lymphocytes by an antigen, those lymphocytes specific for the antigen undergo clonal amplification.

T lymphocytes are formed in the bone marrow, migrate to and mature in the thymus and then enter the peripheral blood and lymphatic circulation. T lymphocytes are subdivided into three distinct types of cells: helper T cells, suppressor T cells, and cytotoxic T cells. T lymphocytes, unlike B lymphocytes, do not produce antibody molecules, but express a heterodimeric cell surface receptor that recognizes peptide fragments of antigenic proteins that are attached to proteins of the major histocompatibility complex (MHC) and expressed on the surfaces of target cells. T lymphocytes include tumor-infiltrating lymphocytes.

Cytotoxic T lymphocytes (CTL) are well known in the art and are typically of the CD3+, CD8+, CD4− phenotype. They typically lyse cells that display fragments of foreign antigens associated with class I MHC molecules on their cell surfaces. CTL typically recognize normal cells expressing antigens after infection by viruses or other pathogens; and tumor cells that have undergone transformation and are expressing mutated proteins or are over-expressing normal proteins.

Natural Killer (NK) cells are well known in the art. NK cells are a subset of lymphocytes active in the immune system and representing an average 15% of mononuclear cells in human peripheral blood. Among the surface markers used to identify human NK cells is a receptor binding with low affinity to the Fc fragment of IgG antibodies, such as Fc-gamma receptor III or CD16 antigen. NK cells have been demonstrated to play an important role in vivo in the defense against tumors, tumor metastases, virus infection, and to regulate normal and malignant hematopoiesis.

Lymphokine-activated killer (LAK) cells are well known in the art and are a cytotoxic population of cells which are capable of lysing autologous tumor cells and NK-cell resistant tumor cell lines. Precursors of LAK cells belong to the subpopulation of "null" lymphocytes that bear neither T nor B cell surface markers. In the human these precursor cells are widely found in peripheral blood, lymph nodes, bone marrow and the thoracic duct. The textbook "Cellular and Molecular Immunology, 6th Edition (Abbas et al.) describes LAK cells as "NK cells with enhanced cytolytic activity for tumor cells as a result of exposure to high doses of IL-2." However, LAK cells have also been produced from cells such as T lymphocytes (Whiteside T L, "Isolation of human NK cells and generation of LAK activity" Curr Protoc Immunol. 2001 May).

Lymphocytes (e.g., TIL, CTL, NK cells, and LAK cells) are important components of the host immune response to viruses, bacterial pathogens and tumors. As a result, individuals with congenital, acquired or iatrogenic immunodeficiency diseases may develop life threatening infections or malignancies (for example, SCID, BMT, AIDS, etc.). Furthermore, a tumor can evade even a normal immune system through a combination of self-tolerance and extracellular adenosine production. Cancer patients, patients with an infective disease, and patients with an immunodeficiency may be treated with adoptive immunotherapy involving the transfer of immune cells such as lymphocytes (e.g., TIL, CTL, NK cells, or LAK cells, or a combination thereof).

Immune cells such as lymphocytes (e.g., TIL, CTL, NK cells, and LAK cells) may be isolated using a variety of methods known in the art. For example, one method of isolating CTL is described in U.S. Pat. No. 6,805,861, wherein allo-restricted CTL were generated by in vitro stimulation of native splenocytes with an appropriate antigen. Alternatively, one may obtain CTL using a method described in U.S. Pat. No. 6,531,451, wherein a blood sample containing T-cell precursors is taken from a mammal, and PBLs are purified from such blood sample and are incubated with stimulator cells which express antigenic peptides complexed with the appropriate MHC molecule. Isolation of NK cells is described in U.S. Pat. No. 7,435,596. Specifically, human primary NK cells may be expanded in the presence of a myeloid cell line that has been genetically modified to express membrane bound IL-15 and 4-1BB ligand. LAK cells may be generated, for example, by treating a patient's mononuclear lymphocytes with interleukin-2, as described in U.S. Pat. Nos. 5,002,879, 4,849,329 and 4,690,915. Mononuclear lymphocytes may be collected, for example, by repeated lymphocytophereses using a continuous flow cell separator as described in U.S. Pat. No. 4,690,915. In some embodiments, the immune cells such as lymphocytes (e.g., TIL, CTL, NK cells, or LAK cells) are isolated using an affinity purification step such as FACS, MACS, or batch purification using an antibody against an appropriate surface antigen. In some instances, a clonal population of immune cells such as lymphocytes (e.g., TIL, CTL, NK cells, or LAK cells) is obtained. In other instances, the population is not clonal.

In certain embodiments, an immune response comprises an increase in the number of immune cells such as lymphocytes (e.g., TIL, CTL, NK cells, or LAK cells) specific to a desired antigen. In certain embodiments, an immune response comprises increased activity of immune cells such as lymphocytes (e.g., TIL, CTL, NK cells, or LAK cells) specific to a desired antigen. For example, increased activity of CTL or NK cells might involve increased production of the cytotoxin perforin. In some embodiments, an immune response comprises an increase in the number or activity of tumor-infiltrating lymphocytes (TILs). In some embodiments, an immune response comprises increased IFN-gamma production of test immune cells such as lymphocytes (e.g., TIL, CTL, NK cells, or LAK cells) compared to untreated control cells of the same type (for example, 2-fold greater production than a control cell). In some embodiments, an immune response comprises higher cytotoxicity than a control cell. Cytotoxicity may be measured, for example, against mastocytoma cells using a $^{51}Cr$ assay.

6.3 Adenosine Pathway Receptor Agonists

One disclosure of the present application is that adenosine pathway receptor agonists may be administered in vitro to a population of immune system cells. While not wishing to be bound by theory, administration of the adenosine pathway receptor agonist may slow the expansion of cells sensitive to adenosine, resulting in the preferential expansion of cells resistant to adenosine. Adenosine pathway receptor agonists include agonists that act directly on an adenosine receptor, as well as ones that act upstream or downstream of the receptor to activate the adenosine receptor pathway. Adenosine pathway receptor agonists are well known in the art, and certain adenosine receptor pathway agonists are highlighted here.

In certain embodiments, the adenosine receptor agonist is a Gi-coupled adenosine receptor agonist. In certain embodiments, the adenosine receptor agonist is an agonist of adenosine receptor A1, A2A, A2B, or A3. (The A2A receptor is sometimes referred to as A2AR, the A2B receptor is sometimes referred to A2BR, and so on.) In some instances, the adenosine receptor agonist functions downstream of the adenosine receptor.

Adenosine receptor pathway agonists fall into a few basic categories. They can be adenosine mimetics, agents that prevent the breakdown or degradation of adenosine, adenosine deaminase inhibitors, adenosine kinase inhibitors, agonist of a Gs protein coupled receptor, a cAMP mimetic, an inhibitor of cAMP inactivation, an agonist of adenylate cyclase, and/or adenosine receptor agonists. These categories are not mutually exclusive.

In certain embodiments, the adenosine receptor pathway agonist is adenosine, an adenosine prodrug, or an adenosine mimetic. Adenosine mimetics include N-ethylcarboxamidoadenosine (NECA) (U.S. Pat. No. 5,500,428), Polyadenylic acid (Todd J et al., "Intravascular Adenosine at Reperfusion Reduces Infarct Size and Neutrophil Adherence" Ann Thorac Surg 1996; 62:1364-1372), 2-chloroadenosine (Camosa B G A et al, "The potentiation of the histamine release induced by adenosine in mast cells from guinea pig lung and heart: sharp dependence on the time of preincubation", Pharmacological Research, Volume 41, Number 3, March 2000, pp. 291-297 (7)).

In other embodiments, the adenosine receptor pathway agonist stimulates adenosine synthesis. For example, it may be an activator of an enzyme that converts IMP into AMP (such as adenylosuccinate synthase and adenylosuccinate lyase). It may also be an activator of an enzyme that converts AMP to adenosine, such as 5'-nucleotidase. 5'-nucleotidase is activated by elevated PKC levels, so a PKC activator may be used to increase adenosine levels. Also, certain ions such as $Mn^{2+}$ and zinc activate 5'-nucleotidase. The adenosine receptor pathway agonist may also be an agent that increases the levels of an enzyme involved in adenosine synthesis.

In yet other embodiments, the adenosine receptor pathway agonist prevents the breakdown or degradation of adenosine. Such agents include adenosine kinase inhibitors, adenosine deaminase inhibitors, and adenosine aminohydrolase inhibitors. Examples of adenosine kinase inhibitors are well known in the art and include 5'-amino-5'-deoxyadenosine, 5-iodotubercidin, and 5'-deoxy-5-iodotubercidin, 4-(N-phenylamino)-5-phenyl-7-(5'-deoxyribofuranosyl)pyrrolo[2,3-d] pyrimidine (Wiesner J B et al., "Adenosine Kinase Inhibitors as a Novel Approach to Anticonvulsant Therapy", Pharmacology, Vol. 289, Issue 3, 1669-1677, June 1999); GP3966 (Boyer S et al., "Adenosine Kinase Inhibitors. 5. Synthesis, Enzyme Inhibition, and Analgesic Activity of Diaryl-erythrofuranosyltubercidin Analogues", J. Med. Chem., 48 (20), 6430-6441, 2005. 10.1021/jm0503650 S0022-2623 (05) 00365-1); $P^1,P^5$-Di(Adenosine-5')Pentaphosphate($Ap_5A$) (Kurebayashi N et al., "$P^1,P^5$-Di(Adenosine-5')Pentaphosphate($Ap_5A$) as an Inhibitor of Adenylate Kinase in Studies of Fragmented Sarcoplasmic Reticulum from Bullfrog Skeletal Muscle" J. Biochem, 1980, Vol. 88, No. 3 871-876); certain pyridopyrimidine analogues (Zheng G Z et al., "Pyridopyrimidine analogues as novel adenosine kinase inhibitors" Bioorganic & Medicinal Chemistry Letters, Volume 11, Issue 16, 20 Aug. 2001, Pages 2071-2074); GP-515 (Bulut K et al., "Long-Term Effects of the Adenosine Kinase Inhibitor GP-515 on Hepatic Microcirculation Following Hemorrhagic Shock" European Journal of Trauma, Volume 29, Number 3, June, 2003). Additional adenosine kinase inhibitors are disclosed in U.S. Pat. No. 5,721,356. Adenosine kinase inhibitors also include nucleic acids (such as siRNAs) designed to downregulate adenosine kinase.

Adenosine deaminase inhibitors include erythro-9-(2-hydroxy-3-nonyl)adenine (EHNA) and coformycin (Sandhu G S et al., "Adenosine deaminase inhibitors attenuate ischemic injury and preserve energy balance in isolated guinea pig heart", Am J Physiol Heart Circ Physiol 265: H1249-H1256, 1993); 2'-Deoxycoformycin (Schrier S M et al., Biochem Pharmacol. 2001 Feb. 15; 61(4):417-25). Adenosine deaminase inhibitors are also disclosed in U.S. Pat. No. 5,731,432.

In certain aspects, the adenosine receptor pathway agonist is an agonist of a Gs protein coupled receptor. For example, it may be a small molecule that binds to and activates the Gs protein coupled receptor.

In other embodiments utilizing an adenosine receptor pathway agonist, it can be a cAMP mimetic. Exemplary cAMP mimetics include PKA activators and adenylate cyclase activators. In other embodiments, the A2AR pathway agonist is an inhibitor of cAMP-degradation such as a cAMP phosphodiesterase inhibitor. Exemplary cAMP phosphodiesterase inhibitors include theophylline, denbutyline, XT-44, roflumilast, revizinone, pimobendan, olprinone, cilomilast, piclamilast, hydroxynonyladenine, motapizone, and dipyridamole (PCT application WO02069905A2) the compounds disclosed in (US Patent Application No. US20070117861A1), adenosine-3',5'-cyclic monophosphorothioate Sp-isomer (Sp-cAMP) (Sheriff S. et al., "Hypothalamic administration of cAMP agonist/PKA activator inhibits both schedule feeding and NPY-induced feeding in rats", Peptides, Volume 24, Number 2, February 2003, pp. 245-254 (10)); (Bu)$_2$cAMP, 8-br-cAMP, epinephrine, pituitary adenylate cyclase-activating polypeptide (PACAP) (Bousquet C et al., "cAMP Neuropeptide Agonists Induce Pituitary Suppressor of Cytokine Signaling-3: Novel Negative Feedback Mechanism for Corticotroph Cytokine Action", Molecular Endocrinology 15 (11): 1880-1890); and dbcAMP (Huang Y H et al., "Signals of seminal vesicle autoantigen suppresses bovine serum albumin-induced capacitation in mouse sperm" Biochemical and Biophysical Research Communications Volume 338, Issue 3, 23 Dec. 2005, Pages 1564-1571).

In certain embodiments, the adenosine receptor pathway agonist stimulates adenylate cyclase activity. Such adenosine receptor pathway agonists include forskolin and forskolin analogues (described in Laurenza A et al., "Stimulation of adenylate cyclase by water-soluble analogues of forskolin" Molecular Pharmacology Volume 32, Issue 1, pp. 133-139, Jul. 1, 1987). Other such agonists include guanosine 5'-[βγ-imido]triphosphate, p[NH]ppG, fluoride. Yet other such agonists include oxymetazoline, UK-14304, BHT-933, BHT-920 (Eason M G et al., "Contribution of ligand structure to activation of alpha 2-adrenergic receptor subtype coupling to Gs", Volume 45, Issue 4, pp. 696-702, Jul. 1, 1994).

In certain embodiments, the adenosine receptor pathway agonist is an adenosine receptor agonist such as an agonist of A1R, A2AR, A2BR, or A3R. In certain embodiments, the adenosine pathway agonist is a small molecule that binds A2AR or A2BR. This binding may be covalent or noncovalent. In certain embodiments, the A2AR pathway agonist is a selective agonist of A2AR. For instance, a selective A2AR pathway agonist may activate A2AR 2-fold, 5-fold, 10-fold, 20-fold, 50-fold, 100-fold, 200-fold, 500-fold, or 1000-fold or more strongly than it activates A1 or A3. In certain embodiments, the A2BR pathway agonist is a selective agonist of A2BR. For instance, a selective A2BR pathway agonist may activate A2BR 2-fold, 5-fold, 10-fold, 20-fold, 50-fold, 100-fold, 200-fold, 500-fold, or 1000-fold or more strongly than it activates A1 or A3.

Figure 3:
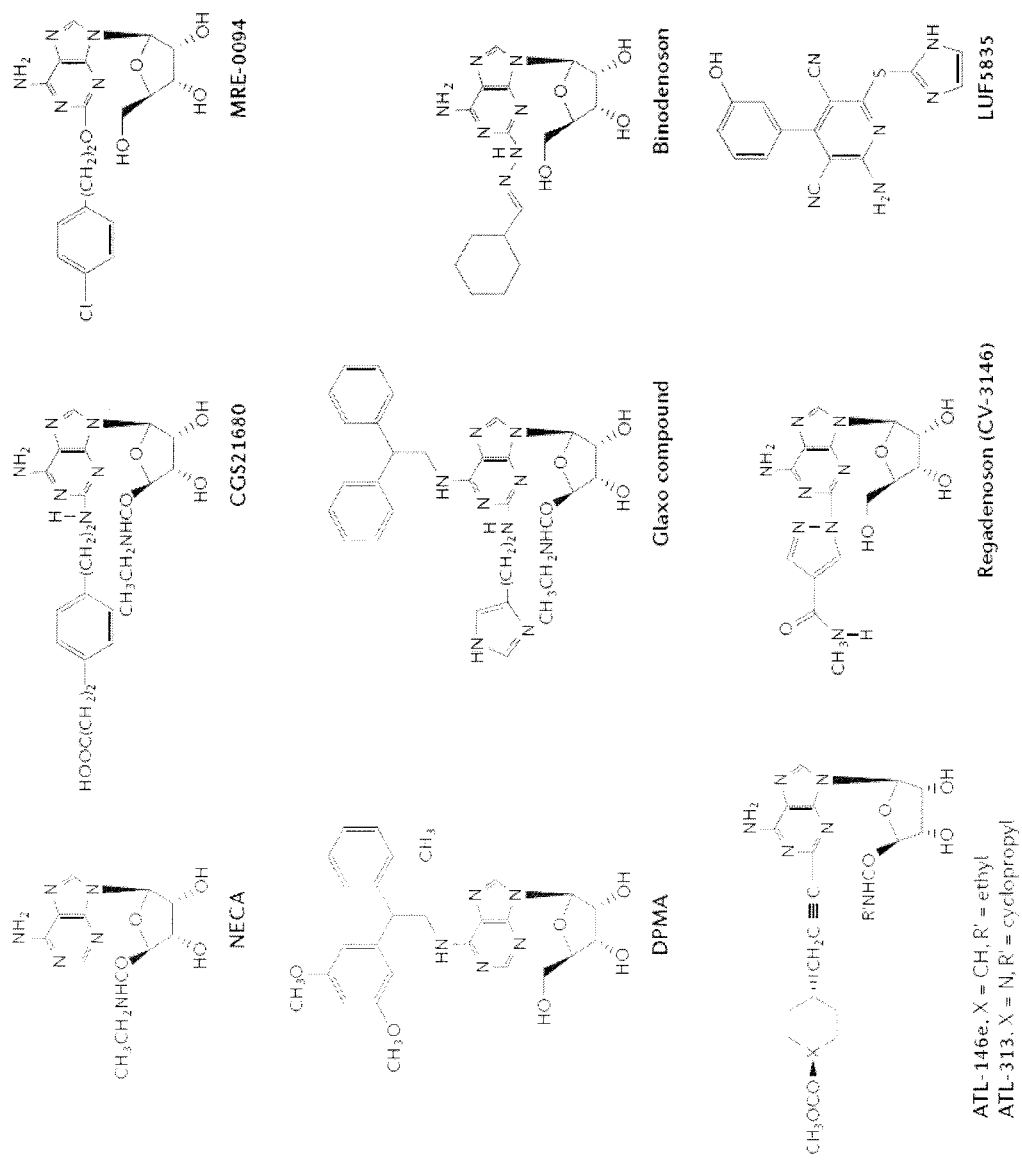
FIG. 3 depicts certain A2AR agonists.
Figure 4:
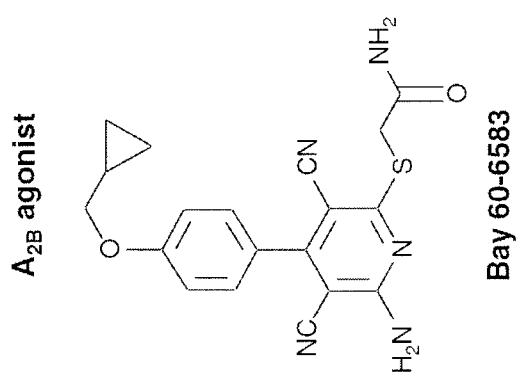
FIG. 4 depicts BAY 60-6583, an A2B agonist.

Certain adenosine A2A receptor agonists useful in the methods herein may be selected from the group consisting of 2-phenylaminoadenosine, 2para-2-carboxyethylphenylamino-5'N-ethylcarboxamido-adenosine, 5'N-ethylcarboxamidoadenosine, 51N-cyclopropyladenosine, 5'N-methylcarboxyamidoadenosine and PD-125944 (for chemical structures, see Bruns, R. F., Ann. N.Y. Acad. Sci. 603:211-226 (1990) at page 216). Other exemplary A2AR agonists include NECA, CGS21680, MRE-0094, DPMA, Glaxo compound (structure provided in FIG. 3), Binodenoson (MRE-0470), ATL-146e (4-[3-[6-amino-9-(5-ethylcarbamoyl-3,4-dihydroxy-tetrahydro-furan-2-yl)-9H-purin-2-yl]-prop-2-ynyl]-cyclohexanecarboxylicacid methyl ester), regadenoson (CVT3146), ATL-313, GW328267X, CV-3146, CVT-3033, LUF5835, Apadenoson, CGS 22492C, and MRA470. The structures of certain of these A2AR agonists are illustrated in FIG. 3. Other adenosine pathway drugs that may be used in accordance with the methods herein include those produced by Adenosine Therapeutics LLC (ATL1222, ATL844, ATL9844, ATL908, ATL902, ATL202, and ATL359). Additional A2AR agonists include 2-[(2-aminoethylamino)carbonylethylphenylethylamino [-5'-N-ethylcarboxamidoadenosine (APEC), N6-cyclohexyladenosine (CHA) (Nikodijevic O, "Behavioral effects of A1- and A2-selective adenosine agonists and antagonists: evidence for synergism and antagonism", Journal of Pharmacology, and Experimental Therapeutics, Volume 259, Issue 1, pp. 286-294, Oct. 1, 1991), and 6-[(2,2-diphenylethyl)amino]-9-(N-ethyl-beta-D-ribofuranosyluronamide)-N-(2-{N'-[1-(2-pyridyl)-4-piperidyl] ureido}ethyl)-9H-purine-2-carboxamide (European Patent No. EP1456219A1; Pfizer), 2-[(cyclohexylmethylene)hydrazino]adenosine (MRE-0470) (Martin P L et al., "Pharmacology and toxicology of the A2A-adenosine receptor agonist 2-[(cyclohexylmethylene)hydrazino]adenosine (MRE-0470) in the rat" Drug Development Research, Volume 42, Issue 2, Pages 76-85). Additional A2AR agonists are described in the following publications: U.S. Pat. No. 6,495,528, WO9967266A1, WO05116037A1, WO07009757A1, WO07059949A1 (assigned to Glaxo); WO8803147A1, U.S. Pat. No. 4,657,897, U.S. Pat. No. 4,657,898, U.S. Pat. No. 4,755,594, U.S. Pat. No. 4,714,697, U.S. Pat. No. 4,673,670, U.S. Pat. No. 4,614,732, U.S. Pat. No. 4,764,506, U.S. Pat. No. 4,683,223, U.S. Pat. No. 4,636,493, U.S. Pat. No. 4,600,707, U.S. Pat. No. 4,791,103, U.S. Pat. No. 4,780,464 (assigned to Warner-Lambert Co.); U.S. Pat. No. 7,238,676, U.S. Pat. No. 6,921,753, US20050124574A1, U.S. Pat. No. 6,900,309, US20040229838A1, US20040229838A1, U.S. Pat. No. 6,624,158, U.S. Pat. No. 6,525,032, U.S. Pat. No. 6,448,236, WO0222630A1, U.S. Pat. No. 6,350,735, WO0200676A1, WO0160835C1, WO0160835A1, WO0127131A1, WO0127130A1, WO0077018A3, WO0077018A2, U.S. Pat. No. 4,738,954, U.S. Pat. No. 4,501,735, U.S. Pat. No. 4,663,311, U.S. Pat. No. 4,616,003, WO8803148A3, U.S. Pat. No. 4,837,207, WO03048180A1, WO02096462A1, U.S. Pat. No. 6,326,359, WO0023457A1 (assigned to Pfizer), WO06023272A1, WO06028618A1, WO03029264A3, WO05107463A1, WO9934804A1, WO0078774A3, WO0078774A2, WO0072799A3, U.S. Pat. No. 5,877,180, U.S. Pat. No. 6,448,235, US20080027022A1, WO07120972A3, US20070265440A1, U.S. Pat. No. 7,226,913, WO03086408A1, US20080064653A1, U.S. Pat. No. 5,075,290 (assigned to the University of Virginia), U.S. Pat. Nos. 7,183,264, 7,144,872, 7,109,180, 6,770,634, 6,642,210, 6,440,948, 6,403,567, 6,214,807, 6,180,615, 20070207978, 20070203090, 20060052332, 20040198692, 20040038928, 20040038928 (assigned to CV Therapeutics).

A number of other A2A receptor agonists have been described, such as substituted 4'-carboxamido and 4'-thioamido adenosine derivatives, in International Patent Application Nos. WO94/17090, WO96/02553, WO96/02543. Also, certain selective A2AR agonists are described in International Patent Application Nos. WO98/28319, WO99/38877, WO99/41267, WO99/67263, WO99/67264, WO99/67265 and WO99/67266 (assigned to GlaxoSmithKlein), WO00/23457, WO00/77018, WO01/94368 and WO02/00676 (assigned to Pfizer). A2A receptor agonists have also been described in WO00/78776, WO00/78777, WO00/78778 and WO00/78779 (CV Therapeutics) and in WOOO/72799 and U.S. Pat. No. 5,877,180 (University of Virginia Foundation).

In certain embodiments, the A2AR agonist is: N-({9-[(2R,3R,4S,5R)-3,4-dihydroxy-5-(methoxymethyl)tetrahydro-2-furanyl-6[(2,2-diphenylethyl)amino]-9H-purin-2-yl}methyl)-2-methyl-1-propanesulfonamide (Example 15 of WO-A-00/23457); 15 cis-(2R,3R,4S,5R)-2-(6-[(2,2-diphenylethyl)amino]-2-{[(4 isopropylcyclohexyl)amino]methyl}-9H-purin-9-yl)-5-(methoxymethyl)tetrahydro 3,4-furandiol and trans-(2R,3R,4S,5R)-2-(6-[(2,2-diphenylethyl)amino]-2-{[(4 isopropylcyclohexyl)amino] methyl}-9H-purin-9-yl)-5-(methoxymethyl)tetrahydro 3,4-furandiol (Example 17 of WO-A-00/23457); 20 N-({9-[(2R,3R,4S,5R)-3,4-dihydroxy-5-(hydroxymethyl)tetrahydro-2- furanyl]-6[(2,2-diphenylethyl)amino]-9H-purin-2-yl}methyl)-2-methyl-1-propanesulfonamide (Example 1 of WO-A-01/27130); (2S,3S,4R,5R)-5-(6-[(2,2-diphenylethyl)amino]-2 {[(isopropylsulfonyl)amino]methyl}-9H-purin-9-yl)-N-ethyl-3,4-dihydroxytetrahydro 2-furancarboxamide (Example 3 of WO-A-01/27131); 9-[(2R,3R,4S,5R)-3,4-dihydroxy-5-(hydroxymethyl)tetrahydro-2-furanyl]-6-[(2,2 diphenylethyl)amino]-N-[2-(1-piperidinyl)ethyl]-9H-purine-2-carboxamide (Example 1 of WO-A-00/77018); 6-[(2,2-diphenylethyl)amino]-9-{(2R,3R,4S,5S)-5-[(ethylamino) carbonyl] 30-3,4-dihydroxytetrahydro-2-furanyl}-N-[2-(1-piperidinyl)ethyl]-9H-purine-2 carboxamide (Example 1 of WO-A-01/60835); N-({9-[(2R,3R,4S,5R)-3,4-dihydroxy-5-(hydroxymethyl)tetrahydro-2-furanyl]-6 1(2,2-diphenylethyl)amino]-9H-purin-2-yl}methyl)-N'-2 (diisopropylamino)ethyl]urea (Example of WO-A-02/00676); or 6-[(2,2-diphenylethyl)amino]-9-{(2R,3R,4S,5S)-5-[(ethylamino) carbonyl]-3,4-dihydroxytetrahydro-2-furanyl}-N-{2-[({[1-(2-pyridinyl)-4-piperidinyl]amino}carbonyl)amino]ethyl}-9H-purine-2-carboxamide (Example 8 of 5 or a pharmaceutically acceptable salt or solvate thereof.

A number of A2AR agonists, and methods of making them, are described in U.S. Patent Application No. US20070270373A1, such as compound I below:

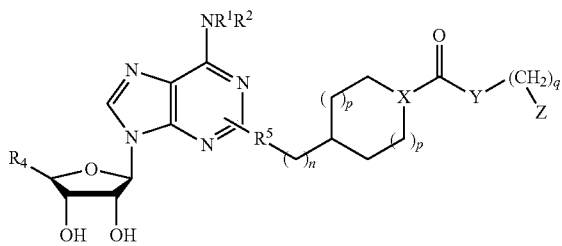

(I)

wherein:

$R^1$ and $R^2$ independently are selected from the group consisting of H, $(C_1-C_8)$alkyl, $(C_3-C_8)$cycloalkyl, $(C_3-C_8)$cycloalkyl$(C_1-C_8)$alkylene, aryl, aryl$(C_1-C_8)$alkylene, heteroaryl, heteroaryl$(C_1-C_8)$alkylene-, diaryl$(C_1-C_8)$alkylene, and diheteroaryl$(C_1-C_8)$alkylene, wherein the aryl and heteroaryl rings are optionally substituted with 1-4 groups independently selected from fluoro, chloro, iodo, bromo, methyl, trifluoromethyl, and methoxy;

each R independently is selected from the group consisting of H, $C_1-C_4$ alkyl, cyclopropyl, cyclobutyl, and $(CH_2)_a$cyclopropyl;

X is CH or N, provided that when X is CH then Z cannot be substituted with halogen, $C_1-C_6$ alkyl, hydroxyl, amino, or mono- or di-$(C_1-C_6$-alkyl)amino;

Y is selected from the group consisting of O, $NR^1$, $OCH_2CH_2O)_mCH_2$—, and —$(NR^1CH_2CH_2O)_mCH_2$—, provided that when Y is O or $NR^1$, then at least one substituent is present on Z;

Z is selected from the group consisting of 5-membered heteroaryl, 6-membered aryl, 6-membered heteroaryl, carbocyclic biaryl, and heterocyclic biaryl, wherein the point of attachment of Y to Z is a carbon atom on Z, wherein Z is substituted with 0-4 groups independently selected from the group consisting of F, Cl, Br, I, $(C_1-C_4)$alkyl, —$(CH_2)_a$$OR^3$, —$(CH_2)_aNR^3R^3$, —NHOH, —$NR^3NR^3R^3$, nitro, —$(CH_2)_aCN$, —$(CH_2)_aCO_2R^3$, —$(CH_2)_aCONR^3R^3$, trifluoromethyl, and trifluoromethoxy;

alternatively, Y and Z together form an indolyl, indolinyl, isoindolinyl, tetrahydroisoquinolinyl, or tetrahydroquinolinyl moiety wherein the point of attachment is via the ring nitrogen and wherein said indolyl, indolinyl, isoindolinyl, tetrahydroisoquinolinyl, or tetrahydroquinolinyl moiety, which is substituted with 0-4 groups independently selected from the group consisting of F, Cl, Br, I, $C_1-C_4$ alkyl, —$(CH_2)_aOR^3$, —$(CH_2)_aNR^3R^3$, —NHOH, —$NR^3NR^3R^3$, $NO_2$, —$(CH_2)_aCN$, —$(CH_2)_aCO_2R^3$, —$(CH_2)_aCONR^3R^3$, $CF_3$, and $OCF_3$;

$R^3$ is independently selected from the group consisting of H, $(C_1-C_6)$alkyl, cycloalkyl, aryl, and heteroaryl;

$R^4$ is selected from the group consisting of $CH_2OR$, $C(O)NRR$, and $CO_2R$;

$R^5$ is selected from the group consisting of $CH_2CH_2$, $CH=CH$, and $C≡C$;

a is selected from 0, 1, and 2;

m is selected from 1, 2, and 3;

n is selected from 0, 1, and 2;

each p independently is selected from 0, 1, and 2; and, q is selected from 0, 1, and 2.

In certain embodiments, the A2AR agonist that is a compound of Formula I above is a compound of Formula Ia:

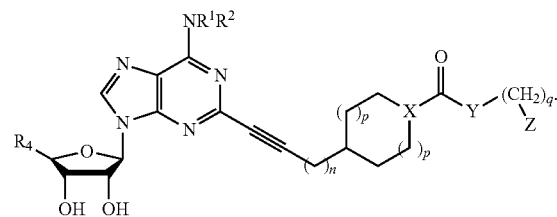

(Ia)

In certain embodiments, the A2AR agonist that is a compound of Formula Ia above is a compound of Formula Ib:

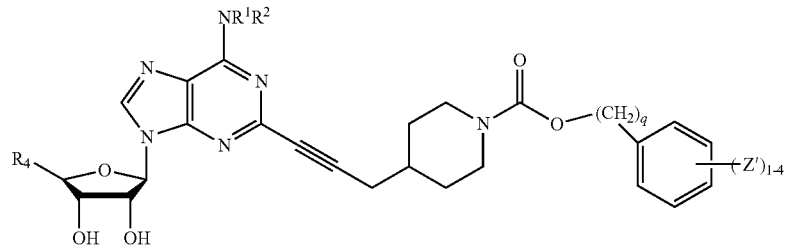

(Ib)

wherein:

each Z' is independently selected from the group consisting F, Cl, Br, I, $C_1$-$C_4$ alkyl, —$(CH_2)_aOR^3$, —$(CH_2)_aNR^3R^3$, —NHOH, —$NW^3NR^3R^3$, $NO_2$, —$(CH_2)_aCN$, —$(CH_2)_aCO_2R^3$, —$(CH_2)_aCONR^3R^3$, $CF_3$, and $OCF_3$.

In certain embodiments, the A2AR agonist that is a compound of Formula Ib above is a compound of Formula Ic:

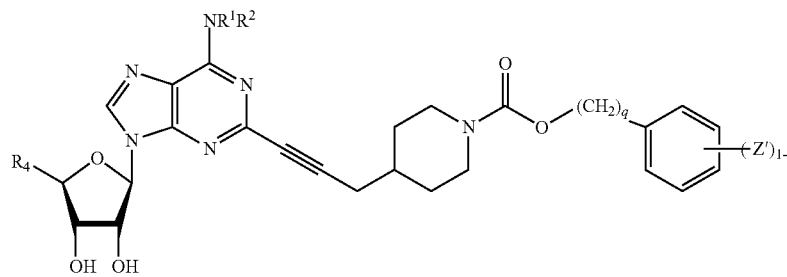

(Ic)

In certain embodiments, Z' is selected from the group consisting of F, Cl, methyl, $OR^3$, $NO_2$, CN, $NR^3R^3$ and $CO_2R^3$. In some embodiments, $R^3$ is methyl or hydrogen.

In other embodiments, the A2AR agonist is an agonist described in US Patent Application No. 20070183995, such as that of Formula III:

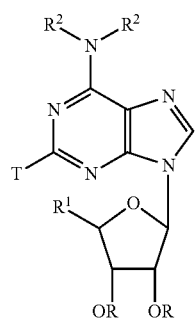

(III)

wherein (a) each R is independently hydrogen, a $C_1$-$C_{20}$ linear, branched, substituted, unsubstituted, saturated and/or unsaturated alkyl, acyl group or aryl group;

(b) $R^1$ is a $C_1$-$C_5$ alkanol or

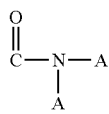

where each A is independently hydrogen or a $C_1$-$C_5$ alkyl; and (c) T is a group comprising at least one heteroatom with the provisos that T has a heteroatom selected from the group consisting of N, O and S bonded to purine and when T is

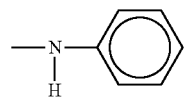

each R and $R^2$ are not simultaneously H when $R^1$ is $CH_2OH$, and when T is

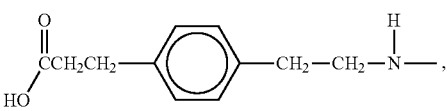

each R and $R^2$ are not simultaneously hydrogen when $R^1$ is

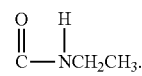

In one embodiment, T is

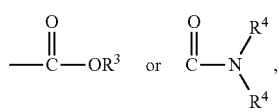

where each $R^2$ is independently (a) hydrogen, a $C_1$-$C_{20}$ linear, branched, cyclic, saturated or unsaturated alkyl group with or without a heteroatom selected from the group consisting of N, O and S, an aryl group, alkyl aryl, $C_4$-$C_9$ heteroaryl, $C_4$-$C_{10}$ heterocycle where the heteroatom is selected from the group consisting of N, O and S, $$-\overset{O}{\underset{}{C}}-OR^3 \quad \text{or} \quad -\overset{O}{\underset{}{C}}-N\overset{R^4}{\underset{R^4}{}},$$

where $R^3$ is a $C_1$-$C_{20}$ linear, branched, saturated or unsaturated alkyl group with or without a heteroatom selected from the group consisting of N, O and S, and each $R^4$ is independently hydrogen, $C_1$-$C_{20}$ linear, branched, saturated or unsaturated alkyl group with or without a heteroatom selected from the group consisting of N, O and S, with the provisos that when T is

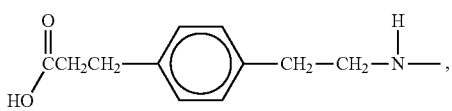

each R and $R^2$ are not simultaneously hydrogen when $R^1$ is

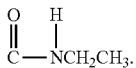

In yet other embodiments, the A2AR agonist is an agonist described in U.S. Pat. No. 6,642,210 (CV Therapeutics), such as compounds of Formula IV:

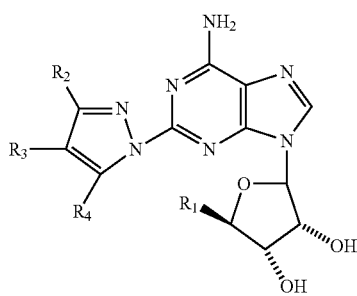

wherein $R^1$=$CH_2OH$;
$R^3$ is selected from the group consisting of $CO_2R^{20}$, —$CONR^7R^8$, and aryl, wherein the aryl substituent is optionally substituted with from 1 to 3 substituents independently selected from the group consisting of halo, alkyl, and $OR^{20}$;
$R^7$ is selected from the group consisting of hydrogen, straight or branched $C_{1-15}$ alkyl and $C_{3-8}$ cycloalkyl, wherein the alkyl substituent is optionally substituted with from 1 to 3 substituents independently selected from the group consisting of aryl and $CO_2R^{20}$, and wherein the optional aryl substituent is optionally substituted with halo;
$R^8$ is selected from the group consisting of hydrogen, straight or branched $C_{115}$ alkyl and $C_{3-8}$ cycloalkyl;
$R^{20}$ is selected from the group consisting of hydrogen and $C_{1-15}$ alkyl;
and wherein $R^2$ and $R^4$ are hydrogen.

In certain embodiments relating to compound IV, $R^3$ is $CO_2R^{20}$; and $R^{20}$ is selected from the group consisting of hydrogen and $C_{1-4}$ alkyl.

In some embodiments, $R^3$ is $CONR^7R^8$;
$R^7$ is selected from the group consisting of hydrogen, straight or branched $C^{1-10}$ alkyl and $C_{3-5}$ cycloalkyl, wherein the alkyl substituent is optionally substituted with from 1 to 2 substituents independently selected from the group consisting of aryl and $CO_2R^{20}$;
$R^8$ is selected from the group consisting of hydrogen, straight and branched $C_{1-3}$ alkyl and $C_{3-5}$ cycloalkyl; and
$R^{20}$ is selected from the group consisting of $C_{1-4}$ alkyl.

In other embodiments relating to formula IV, $R^3$ is aryl, wherein the aryl substituent is optionally substituted with from 1 to 3 substituents independently selected from the group consisting of halo, alkyl and $OR^{20}$; and $R^{20}$ is selected from and the group consisting of $C^{1-4}$ alkyl. Optionally, the compound described in the preceding sentence may be produced such that $R^3$ is aryl, wherein the aryl substituent is phenyl optionally substituted with from 1 to 2 substituents independently selected from the group consisting of chloro, methyl and $OR^{20}$; and $R^{20}$ is methyl.

In some embodiments relating to formula IV, $R^3$ is $CO_2R^{20}$; and $R^{20}$ is selected from the group consisting of hydrogen and $C^{1-4}$ alkyl.

In certain aspects, R 7 is selected from the group consisting of hydrogen, $C_{1-3}$ alkyl and cyclopentyl, wherein the alkyl substituent is optionally substituted with from 1 to 2 substituents, independently selected from the group consisting of phenyl and $CO_2R^{20}$ and wherein each optional phenyl substituent is optionally substituted with halo; $R^8$ is selected from hydrogen and methyl; and $R^{20}$ is selected from hydrogen and ethyl.

In certain embodiments, the compound of Formula IV is selected from the group consisting of ethyl 1-{9-[(4S,2R,3R,5R)-3,4-dihydroxy-5-(hydroxymethyl)oxolan-2-yl]-6-aminopurin-2-yl}pyrazole-4-carboxylate; (4S,2R,3R,5R)-2-{6-amino-2-[4-(4-chlorophenyl)-pyrazolyl]purin-9-yl}-5-(hydroxymethyl)oxolane-3,4-diol; (4S,2R,3R,5R)-2-{6-amino-2-[4-(4-methoxyphenyl)pyrazolyl]purin-9-yl}-5-(hydroxymethyl)oxolane-3,4-diol; (4S,2R,3R,5R)-2-{6-amino-2-[4-(4-methylphenyl)pyrazolyl]purin-9-yl}-5-(hydroxymethyl)-oxolane-3,4-diol; (1-{9-[(4S,2R,3R,5R)-3,4-dihydroxy-5-(hydroxymethyl)oxolan-2-yl]-6-aminopurin-2-yl}pyrazol-4-yl)-N-methylcarboxamide; 1-{9-[(4S,2R,3R,5R)-3,4-dihydroxy-5-(hydroxyrethyl)oxolan-2-yl]-6-aminopurin-2-yl}pyrazole-4-carboxylic acid; (1-{9-[(4S,2R,3R,5R)-3,4-dihydroxy-5-(hydroxymethyl)oxolan-2-yl]-6-aminopurin-2-yl}pyrazol-4-yl)-N,N-dimethylcarboxamide; (1-{9-[(4S,2R,3R,5R)-3,4-dihydroxy-5-(hydroxymethyl)oxolan-2-yl]-6-aminopurin-2-yl}pyrazol-4-yl)-N-ethylcarboxamide; 1-{9-[(4S,2R,3R,5R)-3,4-dihydroxy-5-(hydroxymethyl)oxolan-2-yl]-6-aminopurin-2-yl}pyrazole-4-carboxamide; 1-{9-[(4S,2R,3R,5R)-3,4-dihydroxy-5-(hydroxymethyl)oxolan-2-yl]-6-aminopurin-2-yl}pyrazol-$^4$-yl)-N-(cyclopentyl)carboxamide; (1-{9-[(4S,2R,3R,5R)-3,4-dihydroxy-5-(hydroxymethyl)oxolan-2-yl]-6-aminopurin-2-yl}pyrazol-4-yl)-N-[(4-chlorophenyl)methyl]carboxamide, and ethyl 2-[(1-{9-[(4S,2R,3R,5R)-3,4-dihydroxy-5-(hydroxymethyl)oxolan-2-yl]-6-aminopurin-2-yl}pyrazol-4-yl)carbonylamino]acetate. In certain embodiments, the A2AR agonist is Regadonoson.

In other embodiments, the A2AR agonist is a compound of Formula V, as described in US2006/0135466:

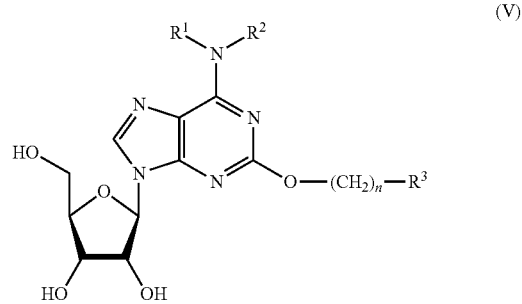

wherein:
$R^1$ and $R^2$ are independently selected from hydrogen, $C_1$-$C_6$alkyl, $C_2$-$C_6$alkenyl, $C_2$-$C_6$alkynyl, $C_3$-$C_8$cycloalkyl, $C_3$-$C_8$cycloalkenyl, $C_7$-$C_{12}$aralkyl, $C_6$-$C_{12}$aryl, 5-7 membered heteroaryl, 4-7 membered heterocycloalkyl, each of which is optionally substituted with 1 to 3 substituents independently selected from the group consisting of hydroxy, $C_1$-$C_6$alkyl, $C_1$-$C_6$alkoxy, amino, mono-($C_1$-$C_6$alkyl)amino, di-($C_1$-$C_6$alkyl)amino, halogen, hydroxy, cyano, nitro, carboxylate, carboxamide, sulfonate, and sulfonamide; or $NR^1R^2$ taken in combination forms a 4-7 membered heterocycloalkyl or a 5-7 membered heteroaryl group, each of which is optionally substituted with 1 to 3 substituents independently selected from the group consisting of hydroxy, $C_1$-$C_6$alkyl, $C_1$-$C_6$alkoxy, amino, mono-($C_1$-$C_6$alkyl)amino, di-($C_1$-$C_6$alkyl)amino, halogen, hydroxy, cyano, nitro, carboxylate, carboxamide, sulfonate, and sulfonamide;

$R^3$ is aryl, cycloalkyl or heteroaryl, each of which is optionally substituted with 1 to 3 substituents independently selected from the group consisting of hydroxy, $C_1$-$C_6$alkyl, $C_1$-$C_6$alkoxy, amino, mono-($C_1$-$C_6$alkyl)amino, di-($C_1$-$C_6$alkyl)amino, halogen, hydroxy, cyano, nitro, carboxylate, carboxamide, sulfonate, and sulfonamide; and n is an integer of 2 or 3.

In certain embodiments, the compound of Formula V is MRE-0094.

In certain embodiments, the A2AR pathway agonist is an adenosine kinase inhibitor such as those described in PCT Publication No. WO9640707A1. For instance, the adenosine kinase inhibitor may be of the general formula VI:

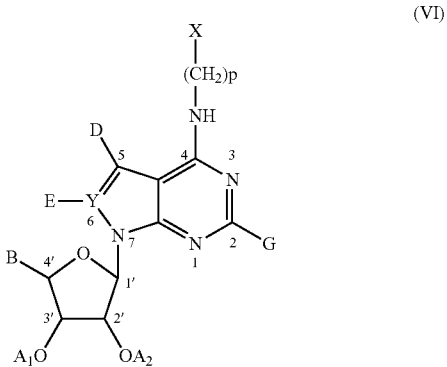

(VI)

wherein:

A1 and A2 are each hydrogen or acyl, or together form a cyclic carbonate;

B is $CH_3$, alkenyl, or $(CH_2)_n$—B', where n is from 1 to 4 and B' is hydrogen, hydroxy, alkyl, alkoxy, amino, azido, halogen, or alkenyl;

D is halogen, alkyl, alkenyl, alkynyl, haloalkyl, cyano, carboxamido, or $(CH_2)_qX$ where q is from 0 to 3;

and each X is independently an aryl group, more preferably an aromatic ring optionally containing a nitrogen, sulfur, or oxygen atom optionally substituted at any position by halogen, alkyl, alkoxy, substituted per halo lower alkyl, sulfonamide, cyano, CONRR' where R and R' are independently hydrogen or lower alkyl, or is a water solubilizing group $(CH_2)_rT$ where r is from 0 to 3 and T is an alkyl or alkenyl chain of 0 to 16 carbon atoms containing a carboxylic acid and optionally containing one or more nitrogen atoms and optionally one or more oxygen atoms, a 5- or 6-membered nitrogen containing heterocyclic aryl group, N-sulfonylated amino, amidoximo, N-aminoguanidino, amidino, guanidino, acylguanidino, cyclic derivatives of amidines and guanidines, acylated sulfonamide, a 5 or 6 membered alicyclic ring containing a basic nitrogen and optionally one or more oxygen atoms or $CONR_2R_3$ where at least one of $R_2$ and $R_3$ contains an alkyl chain containing one or more basic nitrogen atoms and optionally oxygen or taken together form a 5- or 6-membered ring containing at least one basic nitrogen.

Y is carbon or nitrogen;

E is nothing when Y is nitrogen, and is hydrogen or halogen when Y is carbon;

G is hydrogen or halogen;

p is from 0 to 3, preferably 0;

provided at least one X includes a water solubilizing group as defined above or a nitrogen containing heterocycle;

and pharmaceutically acceptable salts thereof.

In some aspects, the adenosine pathway agonist is a specific A2B receptor agonist. In certain embodiments, the A2B receptor agonist is a small molecule that binds the A2B receptor. For example, the A2B receptor agonist may be LUF5835, LUF5845, PHPNECA, para substituted 1,3-dialkyl-8-phenylxanthines, 8-[4-[(N-(2-hydroxyethyl)carboxamidomethyl)oxy]phenyl]-1-propylxanthine, BAY 60-6583, or NECA. Other exemplary A2BR agonists include BAY 60-6583 ([2-[6-amino-3,5-dicyano-4-[4-(cyclopropylmethoxy)-phenyl]pyridin-2-ylsulfanyl]acetamide]) (described in Eckle T et al., J Clin Invest. 2008 Oct. 1; 118 (10): 3301-3315), 2-phenylaminoadenosine (CV1808) (Tostes R C et al., J Pharmacol Exp Ther. 2007 August; 322 (2):678-85.). Additional A2B receptor agonists are described in U.S. Pat. No. 7,135,486 and US Patent Application 20060264432 (Substituted 2-thio-3,5-dicyano-4-aryl-6-aminopyridines).

A number of 2,N(6),5'-substituted A2BR agonists are disclosed in Adachi H et al. (J Med Chem. 2007 Apr. 19; 50 (8):1810-27.) Also, various N(6)-[(hetero)aryl/(cyclo)alkyl-carbamoyl-methoxy-phenyl]-(2-chloro)-5'-N-ethylcarboxamido-adenosines that are A2BR agonists are disclosed in Baraldi P G et al. (Bioorg Med Chem. 2007 Apr. 1; 15 (7): 2514-27.) Another A2BR pathway agonist is 8-(4-chlorophenylthio)-guanosine 3',5'-cyclic monophosphate (CPT) (Kuno A et al., Am J Physiol Heart Circ Physiol. 2008 September; 295 (3):H1288-H1295). BAY 60-6583 and related A2B agonists are described in PCT publication number WO01/25210 and U.S. Pat. No. 7,045,631. The latter describes the following class of compounds:

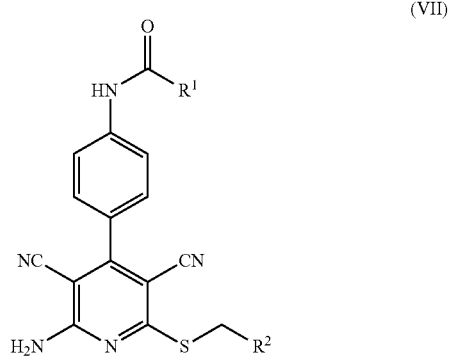

(VII)

in which $R^1$ denotes ($C_1$-$C_4$)-alkyl, ($C_1$-$C_4$)-alkoxy, mono- or di-($C_1$-$C_4$)-alkylamino, and $R^2$ denotes pyridyl or thiazolyl, which radicals can be substituted by halogen, amino or ($C_1$-$C_4$)-alkyl, or a salt, hydrate, or hydrate of the salt thereof.

In certain embodiments, the adenosine receptor pathway agonist reduces the activity of an inhibitor of an adenosine receptor pathway. The inhibitor of the adenosine receptor pathway may be adenosine kinase or adenosine deaminase. The adenosine receptor pathway agonist may also be an activator of an adenosine synthesizing enzyme such as endoN-Tase. Other adenosine synthesizing enzymes include CD39 and CD73. The adenosine receptor pathway agonist may inhibit an enzyme that degrades adenosine, such as adenosine kinase or adenosine deaminase.

A drug can be readily determined if it is an adenosine receptor pathway agonist. For example, one may use known techniques to compare the binding of a radiolabeled putative adenosine receptor agonist to a cell membrane that has adenosine receptor, in the presence of known and unlabeled adenosine receptor antagonist. Alternatively, one may use published methods for evaluating effects of a putative adenosine receptor agonist as competitor against a known radiolabeled adenosine receptor agonist, for binding to cell membranes that have the adenosine receptor. In addition, one may use known techniques to compare the effect of the putative adenosine receptor agonist on cAMP accumulation in adenosine receptor-expressing cells to the effect of a known adenosine receptor antagonist on cAMP accumulation in the same type of cell.

Different adenosine receptor genes have multiple exons and may be subject to alternative splicing. In addition, the A2A receptor gene has at least four alternative promoters. Thus, there may be multiple adenosine receptor isoforms. The compositions and methods herein may relate to all adenosine receptor isoforms, or to a specific subset of them.

6.4 Antisense Nucleic Acids

One way to produce cells insensitive to adenosine is to administer to cells an antisense nucleic acid that reduces expression of the adenosine receptor. There are various antisense technologies available to the skilled artisan.

RNA interference (RNAi) is a phenomenon describing double-stranded (ds)RNA-dependent gene specific posttranscriptional silencing. Initial attempts to harness this phenomenon for experimental manipulation of mammalian cells were foiled by a robust and nonspecific antiviral defense mechanism activated in response to long dsRNA molecules. Gil et al. Apoptosis 2000, 5:107-114. The field was significantly advanced upon the demonstration that synthetic duplexes of 21 nucleotide RNAs could mediate gene specific RNAi in mammalian cells, without invoking generic antiviral defense mechanisms. Elbashir et al. Nature 2001, 411:494-498; Caplen et al. Proc Natl Acad Sci 2001, 98:9742-9747. As a result, small-interfering RNAs (siRNAs) and micro RNAs (miRNAs) have become powerful tools to dissect gene function. The chemical synthesis of small RNAs is one avenue that has produced promising results. Numerous groups have also sought the development of DNA-based vectors capable of generating such siRNA within cells. Several groups have recently attained this goal and published similar strategies that, in general, involve transcription of short hairpin (sh) RNAs that are efficiently processed to form siRNAs within cells. Paddison et al. PNAS 2002, 99:1443-1448; Paddison et al. Genes & Dev 2002, 16:948-958; Sui et al. PNAS 2002, 8:5515-5520; and Brummelkamp et al. Science 2002, 296:550-553. These reports describe methods to generate siRNAs capable of specifically targeting numerous endogenously and exogenously expressed genes.

An RNAi construct typically contains a nucleotide sequence that hybridizes under physiologic conditions of the cell to the nucleotide sequence of at least a portion of the mRNA transcript for the gene to be inhibited (i.e., the "target" gene). The RNAi construct need only be sufficiently similar to natural RNA that it has the ability to mediate RNAi. Thus, an RNAi construct has the advantage of being able to tolerate sequence variations that might be expected due to genetic mutation, strain polymorphism or evolutionary divergence. Mismatches in the center of the siRNA duplex are most important and may reduce or essentially abolish cleavage of the target RNA. In contrast, nucleotides at the 3' end of the siRNA strand that is complementary to the target RNA do not significantly contribute to specificity of the target recognition.

Sequence identity may be optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). Greater than 90% sequence identity, or even 100% sequence identity, between the antisense nucleic acid and the portion of the target gene is preferred. Alternatively, the duplex region of the antisense nucleic acid may be defined functionally as a nucleotide sequence that is capable of hybridizing with a portion of the target gene transcript (e.g., 400 mM NaCl, 40 mM PIPES pH 6.4, 1 mM EDTA, 50° C. or 70° C. hybridization for 12-16 hours; followed by washing).

Production of antisense nucleic acids can be carried a number of methods. For example, an antisense nucleic acid can be produced by chemical synthetic methods or by recombinant nucleic acid techniques. Endogenous RNA polymerase of the treated cell may mediate transcription in vivo, or cloned RNA polymerase can be used for transcription in vitro. Antisense nucleic acids may include modifications to either the phosphate-sugar backbone or the nucleoside, e.g., to reduce susceptibility to cellular nucleases, improve bioavailability, improve formulation characteristics, and/or change other pharmacokinetic properties. For example, the phosphodiester linkages of natural RNA may be modified to include at least one of a nitrogen or sulfur heteroatom. Modifications in RNA structure may be tailored to allow specific genetic inhibition while avoiding a general response to dsRNA. Likewise, bases may be modified to block the activity of adenosine deaminase. Antisense nucleic acids may be produced enzymatically or by partial/total organic synthesis, any modified ribonucleotide can be introduced by in vitro enzymatic or organic synthesis.

Methods of chemically modifying RNA molecules can be adapted for modifying RNAi constructs (see, for example, Heidenreich et al. (1997) Nucleic Acids Res, 25:776-780; Wilson et al. (1994) J Mol Recog 7:89-98; Chen et al. (1995) Nucleic Acids Res 23:2661-2668; Hirschbein et al. (1997) Antisense Nucleic Acid Drug Dev 7:55-61). Merely to illustrate, the backbone of an RNAi construct can be modified with phosphorothioates, phosphoramidate, phosphodithioates, chimeric methylphosphonate-phosphodiesters, peptide nucleic acids, 5-propynyl-pyrimidine containing oligomers or sugar modifications (e.g., 2'-substituted ribonucleosides, a-configuration).

In certain embodiments, the RNAi constructs are "siRNAs." These nucleic acids are between about 19-35 nucleotides in length, and sometimes 21-23 nucleotides in length, e.g., corresponding in length to the fragments generated by nuclease "dicing" of longer double-stranded RNAs. The siRNAs are understood to recruit nuclease complexes and guide the complexes to the target mRNA by pairing to the specific sequences. As a result, the target mRNA is degraded by the nucleases in the protein complex or translation is inhibited. In a particular embodiment, the 21-23 nucleotides siRNA molecules comprise a 3' hydroxyl group.

In other embodiments, the subject RNAi constructs are "miRNAs." microRNAs (miRNAs) are small non-coding RNAs that direct post transcriptional regulation of gene expression through interaction with homologous mRNAs. miRNAs control the expression of genes by binding to complementary sites in target mRNAs from protein coding genes. miRNAs are similar to siRNAs. miRNAs are processed by nucleolytic cleavage from larger double-stranded precursor molecules. These precursor molecules are often hairpin structures of about 70 nucleotides in length, with 25 or more nucleotides that are base-paired in the hairpin. The RNAse III-like enzymes Drosha and Dicer (which may also be used in siRNA processing) cleave the miRNA precursor to produce an miRNA. The processed miRNA is single-stranded and incorporates into a protein complex, termed RISC or miRNP. This RNA-protein complex targets a complementary mRNA. miRNAs inhibit translation or direct cleavage of target mRNAs. (Brennecke et al., Genome Biology 4:228 (2003); Kim et al., Mol. Cells 19:1-15 (2005).

In certain embodiments, miRNA and siRNA constructs can be generated by processing of longer double-stranded RNAs, for example, in the presence of the enzymes Dicer or Drosha. Dicer and Drosha are RNAse III-like nucleases that specifically cleave dsRNA. Dicer has a distinctive structure which includes a helicase domain and dual RNAse III motifs. Dicer also contains a region of homology to the RDE1/QDE2/ARGONAUTE family, which have been genetically linked to RNAi in lower eukaryotes. Indeed, activation of, or overexpression of Dicer may be sufficient in many cases to permit RNA interference in otherwise non-receptive cells, such as cultured eukaryotic cells, or mammalian (non-oocytic) cells in culture or in whole organisms. Methods and compositions employing Dicer, as well as other RNAi enzymes, are described in U.S. Pat. App. Publication No. 20040086884.

The antisense nucleic acid molecules can be purified using a number of techniques known to those of skill in the art. For example, gel electrophoresis can be used to purify such molecules. Alternatively, non-denaturing methods, such as non-denaturing column chromatography, can be used to purify the antisense nucleic acid molecules. In addition, chromatography (e.g., size exclusion chromatography), glycerol gradient centrifugation, affinity purification with antibody can be used to purify antisense nucleic acid.

In certain embodiments, an antisense nucleic acid is in the form of a hairpin structure (named as hairpin RNA). The hairpin RNAs can be synthesized exogenously or can be formed by transcribing from RNA polymerase III promoters in vivo. Examples of making and using such hairpin RNAs for gene silencing in mammalian cells are described in, for example, Paddison et al., Genes Dev, 2002, 16:948-58; McCaffrey et al., Nature, 2002, 418:38-9; McManus et al., RNA 2002, 8:842-50; Yu et al., Proc Natl Acad Sci USA, 2002, 99:6047-52). In some embodiments, such hairpin RNAs are engineered in cells or in an animal to ensure continuous and stable suppression of a desired gene. It is known in the art that miRNAs and siRNAs can be produced by processing a hairpin RNA in the cell.

In yet other embodiments, a plasmid or other DNA construct is used to deliver the double-stranded RNA, e.g., as a transcriptional product. After the coding sequence is transcribed, the complementary RNA transcripts base-pair to form the double-stranded RNA. The plasmid may integrate into the host genome ("stable transfection") or it may eventually be lost or degraded ("transient transfection"). The DNA construct may be delivered to the cell using any means known in the art including viral infection, electroporation, and transfection.

6.5 Dosage Forms

This application also discloses a pharmaceutical composition comprising a pharmaceutically acceptable carrier and the compositions herein. The pharmaceutical composition may be formulated for systemic or local administration. The pharmaceutical composition may be formulated for (for instance) injection, subdermal administration. The pharmaceutical composition may further comprise at least one of a pharmaceutically acceptable stabilizer, diluent, surfactant, filler, binder, and lubricant.

In many embodiments, the pharmaceutical compositions described herein will incorporate the disclosed compositions to be delivered in an amount sufficient to deliver to a patient a therapeutically effective amount of a composition as part of a prophylactic or therapeutic treatment. The desired concentration of composition will depend on absorption, inactivation, and excretion rates of the drug as well as the delivery rate of the composition. It is to be noted that dosage values may also vary with the severity of the condition to be alleviated. It is to be further understood that for any particular subject, specific dosage regimens should be adjusted over time according to the individual need and the professional judgment of the person administering or supervising the administration of the compositions. Typically, dosing will be determined using techniques known to one skilled in the art.

An effective amount of the compositions described herein refers to the amount of one of the compositions which is capable of treating or preventing a disease. In certain instances the disease is cancer, immunodeficiency, or an infectious disease. An effective amount may be sufficient to prohibit, treat, alleviate, ameliorate, halt, restrain, slow or reverse the progression, or reduce the severity of one of these diseases, in patients who have or are at risk for such a disease. As such, these methods include both medical therapeutic and/or prophylactic (prevention) administration as appropriate.

The compositions provided by this application may be administered to a subject in need of treatment by a variety of conventional routes of administration, including orally, topically, parenterally, e.g., intravenously, subcutaneously or intramedullary. Further, the compositions may be administered by inhalation, intranasally, as a rectal suppository, or using a "flash" formulation, i.e., allowing the medication to dissolve in the mouth without the need to use water. Furthermore, the compositions may be administered to a subject in need of treatment by controlled release dosage forms, site specific drug delivery, transdermal drug delivery, patch (active/passive) mediated drug delivery, by stereotactic injection, or in nanoparticles. The compositions may be administered as various formulations including as microemulsions, nanoemulsions, and in a liposomal formulation.

Suitable Carriers and Other Additives

The compositions may be administered alone or in combination with pharmaceutically acceptable carriers, vehicles or diluents, in either single or multiple doses. Suitable pharmaceutical carriers, vehicles and diluents include inert solid diluents or fillers, sterile aqueous solutions and various organic solvents. The pharmaceutical compositions may be formed by combining the compositions and the pharmaceutically acceptable carriers, vehicles or diluents are then readily administered in a variety of dosage forms such as tablets, powders, lozenges, syrups, injectable solutions and the like. These pharmaceutical compositions can, if desired, contain additional ingredients such as flavorings, binders, excipients, additives, a binder, a disintegrating agent, a lubricant, a corrigent, a solubilizing agent, a suspension aid, an emulsifying agent or a coating agent.

Examples of suitable aqueous and non-aqueous carriers which may be employed in the pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity may be maintained, for example, by the use of coating materials, such as lecithin, by the maintenance of the required particle size in the case of dispersions, and by the use of surfactants.

Optionally, one, two, three or more diluents can be added to the formulations disclosed herein. Examples of pharmaceutically acceptable fillers and pharmaceutically acceptable diluents include, but are not limited to, confectioner's sugar, compressible sugar, dextrates, dextrin, dextrose, lactose, mannitol, microcrystalline cellulose, powdered cellulose, sorbitol, sucrose and talc. The filler and/or diluent, e.g., may be present in an amount from about 15% to about 40% by weight of the composition. In certain embodiments, diluents are microcrystalline cellulose which is manufactured by the controlled hydrolysis of alpha-cellulose, obtained as a pulp from fibrous plant materials, with dilute mineral acid solutions. Following hydrolysis, the hydrocellulose is purified by filtration and the aqueous slurry is spray dried to form dry, porous particles of a broad size distribution. Suitable microcrystalline cellulose will have an average particle size of from about 20 nm to about 200 nm. Microcrystalline cellulose is available from several suppliers. Suitable microcrystalline cellulose includes Avicel PH 101, Avicel PH 102, Avicel PH 103, Avicel $P^H$ 105 and Avicel $P^H$ 200, manufactured by FMC Corporation. The microcrystalline cellulose may be present in a tablet formulation in an amount of from about 25% to about 70% by weight. Another appropriate range of this material is from about 30% to about 35% by weight; yet another appropriate range of from about 30% to about 32% by weight. Another diluent is lactose. The lactose may be ground to have an average particle size of between about 50 µm and about 500 µm prior to formulating. The lactose may be present in the tablet formulation in an amount of from about 5% to about 40% by weight, and can be from about 18% to about 35% by weight, for example, can be from about 20% to about 25% by weight.

Optionally one, two, three or more disintegrants can be added to the formulations described herein. Examples of pharmaceutically acceptable disintegrants include, but are not limited to, starches; clays; celluloses; alginates; gums; cross-linked polymers, e.g., cross-linked polyvinyl pyrrolidone, cross-linked calcium carboxymethylcellulose and cross-linked sodium carboxymethylcellulose; soy polysaccharides; and guar gum. The disintegrant, e.g., may be present in an amount from about 2% to about 20%, e.g., from about 5% to about 10%, e.g., about 7% about by weight of the composition. A disintegrant is also an optional but useful component of the tablet formulation. Disintegrants are included to ensure that the tablet has an acceptable rate of disintegration. Typical disintegrants include starch derivatives and salts of carboxymethylcellulose. Sodium starch glycolate is one appropriate disintegrant for this formulation. In certain embodiments, the disintegrant is present in the tablet formulation in an amount of from about 0% to about 10% by weight, and can be from about 1% to about 4% by weight, for instance from about 1.5% to about 2.5% by weight.

Optionally one, two, three or more lubricants can be added to the formulations disclosed herein. Examples of pharmaceutically acceptable lubricants and pharmaceutically acceptable glidants include, but are not limited to, colloidal silica, magnesium trisilicate, starches, talc, tribasic calcium phosphate, magnesium stearate, aluminum stearate, calcium stearate, magnesium carbonate, magnesium oxide, polyethylene glycol, powdered cellulose and microcrystalline cellulose. The lubricant, e.g., may be present in an amount from about 0.1% to about 5% by weight of the composition; whereas, the glidant, e.g., may be present in an amount from about 0.1% to about 10% by weight. Lubricants are typically added to prevent the tableting materials from sticking to punches, minimize friction during tablet compression and allow for removal of the compressed tablet from the die. Such lubricants are commonly included in the final tablet mix in amounts usually less than 1% by weight. The lubricant component may be hydrophobic or hydrophilic. Examples of such lubricants include stearic acid, talc and magnesium stearate. Magnesium stearate reduces the friction between the die wall and tablet mix during the compression and ejection of the tablets. It helps prevent adhesion of tablets to the punches and dies. Magnesium stearate also aids in the flow of the powder in the hopper and into the die. It has a particle size range of 450-550 microns and a density range of 1.00-1.80 g/mL It is stable and does not polymerize within the tableting mix. One lubricant, magnesium stearate may also be employed in the formulation. In some aspects, the lubricant is present in the tablet formulation in an amount of from about 0.25% to about 6%; also appropriate is a level of about 0.5% to about 4% by weight; and from about 0.1% to about 2% by weight. Other possible lubricants include talc, polyethylene glycol, silica and hardened vegetable oils. In an optional embodiment, the lubricant is not present in the formulation, but is sprayed onto the dies or the punches rather than being added directly to the formulation.

Other conventional solid fillers or carriers, such as, cornstarch, calcium phosphate, calcium sulfate, calcium stearate, magnesium stearate, stearic acid, glyceryl mono- and distearate, sorbitol, mannitol, gelatin, natural or synthetic gums, such as carboxymethyl cellulose, methyl cellulose, alginate, dextran, acacia gum, karaya gum, locust bean gum, tragacanth and the like, diluents, binders, lubricants, disintegrators, coloring and flavoring agents could optionally be employed.

An oil component may be a vegetable oil, a synthetic oil, an oil substitute such as triacetin, a mineral oil or a medium chain triglyceride (CT) oil, i.e., a triglyceride oil in which the carbohydrate chain has 8-10 carbon atoms, or MCT oil. Examples of MCT oils include, but are not limited to, TCR™ (trade name of Societe Industrielle des Oleagineaux, France, for a mixture of triglycerides wherein about 95% of the fatty acid chains have 8 or 10 carbons) and MNGLYOL 812™ (trade name of Dynamit Nobel, Sweden, for a mixed triester of glycerine and of caprylic and capric acids). Isopropyl myristate is another commercially available oil. Examples of vegetable oils include, but are not limited to, soybean oil, cotton seed oil, olive oil, sesame oil and castor oil. Mineral oils include, but are not limited to, natural hydrocarbons or their synthetic analogs. Oily fatty acids, such as oleic acid, linoleic acid, various omega-3 fatty acids, fatty alcohols, such as oleyl alcohol, and fatty esters, such as sorbitan monooleate and hydrophobic sucrose esters, may be used as the oil component, although these are not as preferred as the other oils mentioned herein. Other lipids which may be used include, but are not limited to, synthetic and semi-synthetic mono-, di- and/or triglycerides, triglycerides prepared by solvent or thermal fractionation of natural, synthetic or semisynthetic triglycerides, and triglycerides prepared by interesterification and/or directed or random rearrangement.

Additional examples of useful excipients which can optionally be added to the composition are described in the Handbook of Pharmaceutical Excipients, 3rd edition, Edited by A. H. Kibbe, Published by: American Pharmaceutical Association, Washington D.C., ISBN: 0-917330-96-X, or Handbook of Pharmaceutical Excipients ($4^{th}$ edition), Edited by Raymond C Rowe—Publisher: Science and Practice.

Parenteral Administration

A composition as described herein may be administered parenterally (e.g., intravenous, intramuscular, subcutaneous, or intramedullary). Alternatively, formulations described herein may be administered parenterally as drop infusion preparations, or suppositories. For parenteral administration, solutions of the compositions may be prepared in (for example) sesame or peanut oil, aqueous propylene glycol, or in sterile aqueous solutions may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, the sterile aqueous media employed are all readily available by standard techniques known to those skilled in the art.

Certain pharmaceutical compositions disclosed herein suitable for parenteral administration comprise one or more subject compositions in combination with one or more pharmaceutically acceptable sterile, isotonic, aqueous, or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Formulations for rectal or vaginal administration may be presented as a suppository, which may be prepared by mixing a subject composition with one or more suitable non-irritating carriers comprising, for example, cocoa butter, polyethylene glycol, a suppository wax, or a salicylate, and which is solid at room temperature, but liquid at body temperature and, therefore, will melt in the appropriate body cavity and release the encapsulated salt(s) and composition(s). Formulations which are suitable for vaginal administration also include pessaries, tampons, creams, gels, pastes, foams, or spray formulations containing such carriers as are known in the art to be appropriate.

Methods of Preparation

Methods of preparing various pharmaceutical compositions with a certain amount of one or more salts or other active agents are known, or will be apparent in light of this disclosure, to those skilled in this art. For examples of methods of preparing pharmaceutical compositions, see Remington's Pharmaceutical Sciences, Mack Publishing Company, Easton, Pa., 19th Edition (1995). In addition, in certain embodiments, subject compositions of the present application maybe lyophilized or subjected to another appropriate drying technique such as spray drying. Methods of preparing these formulations or compositions include the step of bringing into association subject compositions with the carrier and, optionally, one or more accessory ingredients. In general, the formulations are prepared by uniformly and intimately bringing into association a subject composition with liquid carriers, or finely divided solid carriers, or both, and then, if necessary, shaping the product.

5.6 Methods of Treating Cancer, Immunodeficiency Diseases, and Infections

The cells described herein may be administered to a patient suffering from any impairment in immune activity (such as lymphocyte activity, natural killer cell activity, etc.). For instance, the patient may have a hypoxic tumor that is resistant to untreated immune cells. Alternatively, the patient may suffer from an infectious disease such as a viral infection, bacterial infection, fungal infection, or other eukaryotic cell infection (i.e. protozoal). Diseases with inflammatory pathogenesis typically have tissue microenvironments that are hypoxic and extracellular adenosine rich. Thus, the compositions and methods herein may be used to treat any disease that causes inflammation. The compositions and methods herein may also be used to treat any disease in which there is need to increase the potency of anti-pathogen T cells.

In other embodiments, the patient may have an immunodeficiency, such as a cell type that is unusually sensitive to adenosine of an excess of adenosine. For example, ADA SCID is caused by a deficiency in adenosine deaminase and leads to a toxic buildup of adenosine that prevents T-, B-, and NK-cell cell maturation.

In certain embodiments, the patient has an inflammatory disease, such as asthma, autoimmune diseases (such as multiple sclerosis and rheumatoid arthritis), chronic inflammation, chronic prostatitis, diabetes (including diabetic ulcers) glomerulonephritis, hypersensitivities, inflammatory bowel diseases, pelvic inflammatory disease, reperfusion injury, rheumatoid arthritis, or vasculitis.

When the disease is a viral infection, it may be caused by (for instance) any one of a member of the Adenoviridae family (such as adenovirus), a member of the Coronavirus family (such as SARS), a member of the Picornaviridae family (such as coxsackievirus, hepatitis A virus, or poliovirus), a member of the Herpesviridae family (such as Epstein-Barr virus, herpes simplex, type 1, herpes simplex, type 2, human cytomegalovirus, human herpesvirus, type 8, or varicella-zoster virus), a member of the Hepadnaviridae family (such as hepatitis B virus), a member of the Flaviviridae family (such as hepatitis C virus, yellow fever virus, dengue virus, west Nile virus), a member of the Retroviridae family (such as HIV or HTLV-1), a member of the Orthomyxoviridae family (such as influenza virus), a member of the Paramyxoviridae family (such as measles virus, mumps virus, parainfluenza virus, respiratory syncytial virus), a member of the Papovaviridae family (such as papillomavirus), a member of the Rhabdoviridae family (such as rabies virus), or a member of the Togaviridae family (such as Rubella virus). In certain embodiments, the virus is a ssDNA virus, a dsDNA virus, a ssRNA virus, or a dsRNA virus. The virus may be enveloped or non-enveloped.

In some embodiments, the disease to be treated is cancer; such as any one of breast cancer; bladder cancer; lung cancer; prostate cancer; thyroid cancer; leukaemias and lymphomas such as CML (chronic myelocytic leukaemia), ALL (acute lymphoblastic leukaemia), AML (acute myelocytic leukaemia), PML (pro-myelocytic leukaemia); colon cancer; glioma; seminoma; liver cancer; pancreatic cancer; bladder cancer; renal cancer; cervical cancer; testicular cancer; head and neck cancer; ovarian cancer; neuroblastoma and melanoma.

When the disease is a bacterial infection, it may be an intracellular or extracellular infection. In certain embodiments, the bacterium is *Helicobacter pylori, Chlamydia pneumoniae, Chlamydia trachomatis, Ureaplasma urealyticum, Mycoplasma pneumoniae, Staphylococcus* spp., *Sta-*

*phylococcus aureus, Streptococcus* spp., *Streptococcus pyogenes, Streptococcus pneumoniae, Streptococcus viridans, Enterococcus faecalis, Neisseria meningitidis, Neisseria gonorrhoeae, Bacillus anthracis, Salmonella* spp., *Salmonella typhi, Vibrio cholera, Pasteurella pestis, Pseudomonas aeruginosa, Campylobacter* spp., *Campylobacter jejuni, Clostridium* spp., *Clostridium difficile, Mycobacterium* spp., *Mycobacterium tuberculosis, Treponema* spp., *Borrelia* spp., *Borrelia burgdorferi, Leptospria* spp., *Hemophilus ducreyi, Corynebacterium diphtheria, Bordetella pertussis, Bordetella parapertussis, Bordetella bronchiseptica, hemophilus influenza, Escherichia coli, Shigella* spp., *Erlichia* spp., *Rickettsia* spp.

The subject compositions can also be used in the treatment various human and veterinary parasitic diseases; including human protozoal pathogens such as; amebiasis from *Entamoeba histolytica*, amebic meningoencephalitis from the genus *Naegleria* or *Acanthamoeba*, malaria from *Plasmodium vivax, Plasmodium ovale, Plasmodium malariae*, and *Plasmodium falciparum*, leishmaniasis from such protozoa as *Leishmania donovani, Leishmania infantum, Leishmania chagasi, Leishmania tropica, Leishmania major, Leishmania aethiopica, Leishmania mexicana*, and *Leishmania braziliensis*, Chagas' disease from the protozoan *Trypanosoma cruzi*, sleeping sickness from *Trypanosoma brucei, Trypanosoma gambiense*, and *Trypanosoma rhodesiense*, toxoplasmosis from *Toxoplasma gondii*, giardiasis from *Giardia lamblia*, cryptosporidiosis from *Cryptosporidium parvum*, trichomoniasis from *Trichomonas vaginalis, Trichomonas tenax, Trichomonas hominis*, pneumocystis pneumonia from *Pneumocystis carinii*, bambesosis from *Bambesia microti, Bambesia divergens*, and *Bambesia boris*, and other protozoans causing intestinal disorders such as *Balantidium coli* and *Isospora belli*. The subject compositions would also be useful in treating certain helminthic infections including the species: *Taenia solium, Taenia saginata, Diphyllobothrium lata, Echinococcus granulosus, Echinococcus multilocularis, Hymenolepis nana, Schistosoma mansomi, Schistosoma japonicum, Schistosoma hematobium, Clonorchis sinensis, Paragonimus westermani, Fasciola hepatica, Fasciolopsis buski, Heterophyes heterophyes, Enterobius vermicularis, Trichuris trichiura, Ascaris lumbricoides, Ancylostoma duodenale, Necator americanus, Strongyloides stercoralis, Trichinella spiralis, Wuchereria bancrofti, Onchocerca volvulus, Loa loa, Dracunculus medinensis*, and fungal pathogens such as: *Sporothrix schenckii, Coccidioides immitis, Histoplasma capsulatum, Blastomyces dermatitidis, Paracoccidioides brasiliensis, Candida albicans, Cryptococcus neoformans, Aspergillus fumigatus, Aspergillus flavus*, fungi of the genera *Mucor* and *Rhizopus, Fusarium solani* and species causing chromomycosis such as those of the genera *Phialophora* and *Cladosporium*, and important veterinary protozoal pathogens such as: *Babesia caballi, Babesia canis, Babesia equi, Babesia felis, Balantidium coli, Besnoitia darlingi, Eimeria acervulina, Eimeria adenoeides, Eimeria ahsata, Eimeria alabamensis, Eimeria auburnensis, Eimeria bovis, Eimeria brasiliensis, Eimeria brunetti, Eimeria canadensis, Eimeria cerdonis, Eimeria crandallis, Eimeria cylindrica, Eimeria debliecki, Eimeria despersa, Eimeria ellipsoidalis, Eimeria fauvei, Eimeria gallopavonis, Eimeria gilruthi, Eimeria granulosa, Eimeria hagani, Eimeria illinoisensis, Eimeria innocua, Eimeria intricate, Eimeria leuskarti, Eimeria maxima, Eimeria meleagridis, Eimeria meleagrimitis, Eimeria mitis, Eimeria mivati, Eimeria necatrix, Eimeria neodebliecki, Eimeria ninakohlyakimorae, Eimeria ovina, Eimeria pallida, Eimeria parva, Eimeria perminuta, Eimeria porci, Eimeria praecox, Eimeria punctata, Eimeria scabs, Eimeria spinoza, Zimeria subrotunda, Eimeria subsherica, Eimeria suis, Eimeria tenella, Eimeria wyomingensis, Eimeria zuernii, Endolimax gregariniformis, Endolimax nana, Entamoeba bovis, Entamoeba gallinarum, Entamoeba histolytica, Entamoeba suis, Giardia bovis, Giardia canis, Giardia cati, Giardia lamblia, Haemoproteus meleagridis, Hexamita meleagridis, Histomonas meleagridis, Iodamoeba buetschili, Isospora bahiensis, Isospora burrowsi, Isospora canis, Isospora fells, Isospora ohioensis, Isospora rivolta, Isospora suis, Klossiella equi, Leucocytozoon caallergi, Leucocytozoon smithi, Parahistomonas wenrichi, Pentatrichomonas hominis, Sarcocystis betrami, Sarcocystis bigemina, Sarcocystis cruzi, Sarcocystis fayevi, hemionilatrantis, Sarcocystis hirsuta, Sarcocystis miescheviana, Sarcocystis muris, Sarcocystis ovicanis, Sarcocystis tenella, Tetratrichomonas buttreyi, Tetratrichomonas gallinarum, Theileria mutans, Toxoplasma gondii, Toxoplasma hammondi, Trichomonas canistomae, Trichomonas gallinae, Trichomonas felistomae, Trichomonas eberthi, Trichomonas equi, Trichomonas foetus, Trichomonas ovis, Trichomonas rotunda, Trichomonas suis*, and *Trypanosoma melophagium*.

It will be appreciated that the methods herein may be employed with any mammal such as human, cat, dog, horse, cow, sheep or pig. In some embodiments, the subject is a vertebrate. In certain embodiments, the subject is a mammal.

In yet another aspect, the methods herein feature a step of inducing or enhancing an immune response in a subject in need thereof, comprising administering oxygen to the subject in an amount sufficient to induce or enhance the immune response, wherein the oxygen is administered in a hyperbaric chamber or as supplemental oxygen. Methods of administering oxygen to augment an immune response are described in detail in PCT/US2008/001891, and are summarized here.

In one embodiment, 100% oxygen is administered in a hyperbaric chamber. In certain embodiments, the hyperbaric chamber has an internal pressure that is greater than atmospheric pressure at sea level. In particular embodiments, the internal pressure is about 1.5 times greater than, about 2 times greater than, about 2.5 times greater than, about 3 times greater than, about 3.5 times greater than, about 4 times greater than, or more than about 4 times greater than atmospheric pressure at sea level. In some embodiments, the hyperbaric chamber internal pressure results in an arterial oxygen tension in excess of 1000 mm Hg, in excess of 1500 mm Hg, in excess of 2000 mm Hg, in excess of 2500 mm Hg, or in excess of 3000 mm Hg. In other embodiments, the hyperbaric chamber internal pressure results in an oxygen tension in tissue of about 300 mm Hg, of about 350 mm Hg, of about 400 mm Hg, of about 450 mm Hg, or of about 500 mm Hg.

In one embodiment, the oxygen is administered as supplemental oxygen at a level that is increased relative to the level of ambient oxygen. In some embodiments, the oxygen is administered in a gas mixture that includes oxygen at a level between about 10% and about 100%, between about 20% and about 100%, between about 21% and about 100%, between about 25% and about 100%, between about 30% and about 90%, or between about 40% and about 60%. In certain embodiments, the oxygen is administered at a level that is greater than 21%, greater than 30%, greater than 40%, greater than 45%, greater than 50%, greater than 60%, greater than 70%, greater than 80%, greater than 90%, or greater than 95% oxygen. In one particular embodiment, about 60% oxygen is administered to the subject. In another particular embodiment, about 100% oxygen is administered to the subject.

In some embodiments, the supplemental oxygen is supplied by way of a nasal cannula, a nasal catheter or a transtracheal catheter. In other embodiments, the supplemental oxygen is supplied in a sealed chamber with an internal pressure that is not greater than atmospheric pressure at sea level.

In some embodiments, the oxygen is administered for about 1 hr. to about 4 weeks. In certain embodiments, the oxygen is administered for about 1 hr., for about 1.5 hr., for about 2 hr., for about 3 hr., for about 4 hr., for about 6 hr., for about 8 hr., for about 10 hr., for about 12 hr., for about 24 hr., for about 2 days, for about 4 days, for about 1 week, for about 2 weeks, for about 3 weeks, for about 4 weeks, for about 1 month, for about 2 months, for about 6 months, or for more than 6 months.

In certain embodiments, the oxygen is administered at least once per day. In certain embodiments, the oxygen is administered at least once every hr., at least every 2 hr., at least every 4 hr., at least every 8 hr., at least every 12 hr., at least every 24 hr., at least every day, at least every 2 days, at least every 4 days, at least every week, at least every 2 weeks, at least every 4 weeks, at least every month, at least every 2 months, at least every 4 months, at least every 6 months, or more than 6 months.

In certain embodiments, the oxygen provided is present in a mix of gasses having at least 21%, 25%, 30%, 40%, 45%, 50%, 60%, 70%, 80%, 90%, or essentially 100% oxygen. In certain embodiments, the oxygen is delivered to the patient through a mask that does not require intubation. In certain embodiments, the oxygen is delivered to the patient through a mask that does not require ventilation.

In the methods described herein, oxygen can be administered in a hyperbaric chamber or as supplemental oxygen. The administration of oxygen in a hyperbaric chamber is also referred to as hyperbaric oxygen therapy ("HBOT"). In HBOT, a subject is placed in a hyperbaric chamber and is administered 100% oxygen at a pressure that is greater than atmospheric pressure at sea level. Hyperbaric chambers have been available for many years and are known in the art (see, e.g., U.S. Pat. No. 4,727,870, U.S. Pat. No. 6,016,803, U.S. Pat. No. 6,321,746, U.S. Pat. No. 6,484,716). The methods described herein are not limited to the use of any particular hyperbaric chamber. Hyperbaric chambers can be commercially obtained from, for example, Parry Baromedical Corporation (Riviera Beach, Fla.) or Performance Hyperbarics (Kula, Hi.). Oxygen can also be administered in a hyperbaric chamber at a hyperbaric oxygen facility or clinic. One of ordinary skill in the art would readily appreciate the steps to take to deliver hyperbaric oxygen in accordance with the methods described herein (see, e.g., Tibbles et al., *New England J. Med.* 334:1642-1648, 1996).

In other methods described herein, oxygen is administered as supplemental oxygen. The use of supplemental oxygen is known in the art (see, e.g., Tarpy et al., *N. Engl. J. Med.* 333:710-714, 1995). Generally, supplemental oxygen therapy is administered from an oxygen concentrator or in the form of compressed gas or liquid oxygen. Subjects usually receive oxygen through a nasal cannula, but other devices such as nasal catheters, transtracheal catheters, and electronic demand devices can also be used. One of ordinary skill in the art would readily appreciate how to use and manipulate supplemental oxygen devices to deliver oxygen in accordance with the methods described herein, and these methods are not limited to the use of any particular supplemental oxygen device. For example, oxygen can be administered using a protocol similar to that described in Kabon et al., *Curr. Opin. Anaesthesiol.* 19:11-18, 2006.

In yet other methods described herein, oxygen is administered through a mask. Numerous masks have been described in the art. For example, plastic oxygen masks are frequently used in a health care setting. These masks do not deliver a high concentration of oxygen to the patient. Silicone and rubber masks provide tighter seals than plastic masks, and consequently can deliver a higher concentration of oxygen. Such masks have valves to prevent re-breathing of exhaled carbon dioxide. Such masks are used, for example, by aviators. Silicone and rubber masks can be classified into three main groups: continuous flow masks (which, as the name implies, provide an uninterrupted supply of oxygen), "diluter demand" masks (which provide oxygen only when the user inhales) and "pressure demand" masks (which provide oxygen only when the user inhales and are used when the ambient air pressure is low, for example at very high altitudes). An oxygen mask may be attached to a tank containing compressed oxygen, including liquid oxygen.

In certain embodiments, oxygen is delivered to a patient without mechanical ventilation. In certain embodiments, oxygen is delivered to a patient without intubation.

Oxygen concentration refers to $FiO_2$, or the fractional concentration of oxygen in inspired air, measured as volume per volume. Oxygen can be administered daily or several times a day over a period of a few days to months, or even years. A therapeutically effective amount of oxygen can be the amount of oxygen necessary to stimulate the immune system of a subject. Specific immunostimulatory effects that can be caused by oxygen administration as well as specific immunosuppressive effects that can be caused by oxygen administration are described herein. In some embodiments, an immunostimulatory amount of oxygen is an amount sufficient to stimulate an immune response without causing a substantial cytotoxic effect (such as without killing more than about 10% of cells in a sample).

The subject to whom oxygen is administered can be monitored for one or more signs of oxygen toxicity. For example, a subject can be monitored for one or more of nausea, vomiting, seizures, sweating, pallor, muscle twitching, anxiety, respiratory changes, visual changes, tinnitus, hallucinations, vertigo, hiccups, decreased level of consciousness, dry cough, substernal chest pain, bronchitis, shortness of breath, pulmonary edema, or pulmonary fibrosis. The subject can be monitored at any time, e.g., before, during, and/or after oxygen administration.

In other embodiments, the method further comprises administering a therapeutically effective amount of a therapeutic agent to the subject. In certain embodiments, the therapeutic agent is an oxygen-enhancing substance that increases local oxygen tension in cancerous or otherwise hypoxic tissue in the subject. In some embodiments, the therapeutic agent is an A2A or A2B adenosine receptor antagonist. In some embodiments, the therapeutic agent is a Gi-coupled adenosine receptor agonist. In some embodiments, the therapeutic agent is an inhibitor of extracellular adenosine. In some embodiments, the therapeutic agent is an agent that decreases inflammation-associated local tissue hypoxia or decreases the redox status of molecules in an inflamed local tissue environment.

In certain embodiments, the therapeutic agent is an anti-tumor or anti-cancer agent. In certain embodiments, the anti-tumor or anti-cancer agent selectively targets the cells of the tumor. In particular embodiments, the anti-tumor or anti-cancer agent is a nucleic acid molecule that encodes a protein that promotes apoptosis. In certain embodiments, the anti-tumor or anti-cancer agent is an alkylating drug, a folate antagonist, a purine antagonist, a pyrimidine antagonist, a spindle poison, a podophyllotoxin, an antibiotic, a nitrosurea, an inorganic ion, a biologic response modifier, an enzyme, or a hormone.

In certain embodiments, the adoptive immunotherapy is combined with a second treatment that augments the immune response. The second treatment may be, for example, an adjuvant and/or a cytokine Examples of cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); epidermal growth factor; hepatic growth factor; fibroblast growth factor; prolactin; placental lactogen; tumor necrosis factor-alpha and -beta; mullerian-inhibiting substance; mouse gonadotropin-associated peptide; inhibin; activin; vascular endothelial growth factor; integrin; thrombopoietin (TPO); nerve growth factors such as NGF-alpha; platelet-growth factor; transforming growth factors (TGFs) such as TGF-alpha and TGF-beta; insulin-like growth factor-I and -II; erythropoietin (EPO); osteoinductive factors; interferons such as interferon-alpha, -beta and -gamma colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1alpha, IL-2, IL-3, IL-4, IL-5, IL-6, IL-7, IL-8, IL-9, IL-10, IL-11, IL-12; a tumor necrosis factor such as TNF-alpha or TNF-beta; and other polypeptide factors including LIF and kit ligand (KL). Cytokines include proteins from natural sources or from recombinant cell culture and biologically active equivalents of the native sequence cytokines.

In another aspect, the disclosure provides a method of producing a tumor defense-resistant immune cell or an anti-viral immune cell, comprising culturing an immune cell under hypoxic culture conditions to produce an immune cell that is resistant to hypoxia-produced extracellular adenosine, thereby producing a tumor defense-resistant immune cell or an anti-viral immune cell. In some embodiments, the cell is cultured under hypoxic conditions and in the presence of adenosine or an adenosine pathway agonist. In some embodiments, the immune cell is a cytotoxic T lymphocyte (CTL), NK cell, or a lymphokine-activated killer (LAK) cell. In certain embodiments, the hypoxic culture conditions comprise less than 4% oxygen. In particular embodiments, the hypoxic culture conditions comprise between 0.5% and 5% oxygen, between 1% and 4% oxygen, between 1% and 3% oxygen, or between 1% and 2% oxygen.

In some embodiments, the subject being treated is immunocompromised (or immunodeficient). In certain embodiments, the subject is infected with human immunodeficiency virus (HIV). In other embodiments, the subject is receiving immunosuppressive therapy such as, for example, chemotherapy or radiation therapy. In certain embodiments, the immunocompromised patient suffers from an inherited immunodeficiency such as SCID. In certain embodiments, the subject is infected with a virus, bacterium, or fungus. In certain embodiments, the subject has or is suffering from one or more symptoms of smallpox, yellow fever, distemper, cholera, fowl pox, scarlet fever, diphtheria, tetanus, whooping cough, influenza, rabies, mumps, measles, foot and mouth disease, or poliomyelitis.

In other embodiments, the method further comprises the step of evaluating the subject for a marker of an induced or enhanced immune response. In certain embodiments, the method comprises evaluating the level of expression of immunoglobulin, cytokines, interferon gamma, interferon beta, interferon alpha, IL-12p40, TNF-alpha, or IL-17 mRNA, relative to the level before oxygen administration. In some embodiments, the subject is evaluated before, during, and/or after oxygen administration. In some embodiments, the disclosed therapeutics are administered until a predetermined level of an immune response is achieved.

In some embodiments, the tumor to be treated is greater than about 2 mm in diameter. In certain embodiments, the size of the tumor to be treated is greater than about 0.5 mm in diameter, greater than about 1.0 mm in diameter, greater than about 1.5 mm in diameter, greater than about 2.0 mm in diameter, greater than about 2.5 mm in diameter, greater than about 3.0 mm in diameter, greater than about 4.0 mm in diameter, or greater than about 5.0 mm in diameter.

In some embodiments, the tumor to be treated has localized hypoxia areas. In certain embodiments, the tumor to be treated is a tumor of the kidney, urinary tract, colon, rectum, lung, liver, breast, prostate, or skin, or another tumor that may be recognized by immune cells and that may have tumor-infiltrating T cells.

In some embodiments, the adoptive transfer improves tumor or cancer rejection.

In certain embodiments, the administration of an adenosine receptor agonist to the cell population results in preferential expansion of the cells that express low levels of adenosine receptors. In specific embodiments, the administration of an adenosine receptor agonist to the cell population results in preferential expansion of the cells that express a low activity form of an adenosine receptor.

In certain embodiments, more than one adenosine receptor agonist is administered to the cell population. For example, two adenosine receptor agonists may be administered simultaneously or sequentially. If the agonists are adminstered sequentially, there may or may not be a "wash out phase" between administration of the two agonists, where no adenosine receptor agonist is administered.

In some embodiments, the immune cells administered to a patient show increased tumor-infiltrating activity relative to the patient's untreated immune cells. In one embodiment, the immune cells have an enhanced anti-tumor activity relative to the patient's untreated immune cells. In certain embodiments, the anti-tumor or anti-cancer activity is a cytotoxic activity or a secretion of cytokines. In particular embodiments, the secreted cytokines disrupt the blood supply to the tumor or prevent the formation of new blood vessels that supply blood to the tumor.

In other embodiments, the method of treatment further comprises the step of evaluating the size of the tumor, the volume of the tumor, and/or the number of tumor cells after adoptive immunotherapy. In some embodiments, the size of the tumor, the volume of the tumor, and/or the number of tumor cells are evaluated before, during, and/or after adoptive immunotherapy. In certain embodiments, adoptive immunotherapy is performed until the tumor is reduced to a preselected size, volume, or number of cells.

In one embodiment, adoptive immunotherapy is performed in an amount and for a time to reduce the size of the tumor, the volume of the tumor, and/or the number of tumor cells, compared to the size, volume, and/or number of tumor cells prior to administration of oxygen. In certain embodiments, adoptive immunotherapy reduces the size of the tumor, the volume of the tumor, and/or the number of tumor cells to less than 100%, to less than 95%, to less than 90%, to less than 80%, to less than 70%, to less than 60%, to less than 50%, to less than 30%, or to less than 10% of its size, volume, or cell number prior to therapy. In some embodiments, the adoptive immunotherapy reduces the growth of the tumor. In certain embodiments, the adoptive immunotherapy reduces the growth rate of the tumor by 10%, by 20%, by 30%, by 40%, by 50%, by 60%, by 70%, by 80%, by 90%, or by more than 90%, as compared to the growth rate of the tumor prior to adoptive immunotherapy.

In certain embodiments, the adoptive immunotherapy increases patient survival. In some aspects, the adoptive immunotherapy increases cell death of tumor or cancer cells.

Another aspect provides a method for enhancing treatment of a cancer patient involving performing adoptive immunotherapy and administering one or more of oxygen, an adenosine pathway antagonist or a HIF-1α antagonist, in conjunction with one or more of radiation therapy, ultrasound ablation, thermal ablation, electrical ablation, surgical excision, cryotherapy, laser therapy, phototherapy and the like.

In certain embodiments, the immune cells are administered once every day or every other day for from one to five daily doses. In some embodiments, administration of the first daily dose begins about three, four, or five days after the patient first undergoes leukapheresis to collect the cells. The quantity of immune cells to be administered varies with the patient and the responsiveness of the neoplastic disease state to the treated. The subject compositions may be administered once, or may be divided into a number of smaller doses to be administered at varying intervals of time, depending in part on the release rate of the compositions and the desired dosage.

7. EXAMPLES

7.1 Example 1

Tumors use various means to protect themselves from the anti-tumor activities of immune system. One of the significant self-protective mechanisms is extracellular adenosine in tumor microenvironment, which inactivates anti-tumor effector T cells via signaling through A2A adenosine receptors (A2AR). Indeed, the lack of A2AR signaling led to augmented inflammatory responses and to enhanced tumor rejection. Anti-tumor T cells that are resistant to adenosine-mediated immunosuppression will be of significant benefit to improve the outcome of tumor adoptive immunotherapy.

The induction of cytotoxic T lymphocytes (CTL) in the presence of an adenosine receptor agonist, NECA, was studied. The CTL expanded in the presence of NECA were found to produce much less cAMP than normal CTL in response to adenosine receptor agonists. Furthermore, functional assays including cytokine production and cytotoxicity assay demonstrated that expansion of CTL with NECA made the CTL resistant to the adenosine-induced immunosuppressive mechanism. While not wishing to be bound by theory, this may be because of down-regulation of A2AR in CTL, or negative selection that allows preferential growth of adenosine-resistant CTL.

Next, the efficacy of adenosine-resistant T cells was assayed in eradication of tumors. The lung metastasis model of MCA205 sarcoma was used to compare the effect of NECA-treated anti-tumor T cells with conventional (untreated) T cells. Anti-MCA205 effector cells were induced as follows. MCA205 ($1\times10^6$ cells) were injected s.c. to immunize C57BL/6 mice. After 12 days, tumor draining lymph node (TLDN) cells were collected and stimulated with anti-CD3 mAb for 2 days. The cells were further expanded for 4 more days with IL-2 in the presence or absence of NECA (0.1 μM). Either conventional (untreated) anti-tumor effector cells (TDLN) or NECA-treated effector cells (NECA-TDLN) were adoptively transferred into tumor-bearing mice, which have the established tumors in the lung by intravenous injection of MCA205 ($1\times10^6$ cells) 10 days before the adoptive transfer. Cytotoxic and IFN-γ-producing activities in NECA-TDLN were comparable to normal TDLN (data not shown). The efficacy of adoptive transfer was evaluated by counting the number of nodules in the lung.

Figure 1:
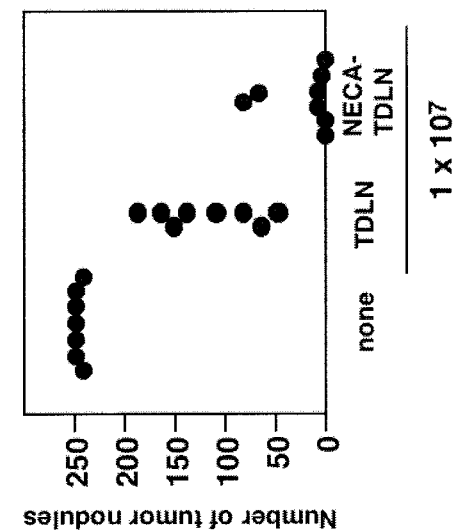
Figure 1:
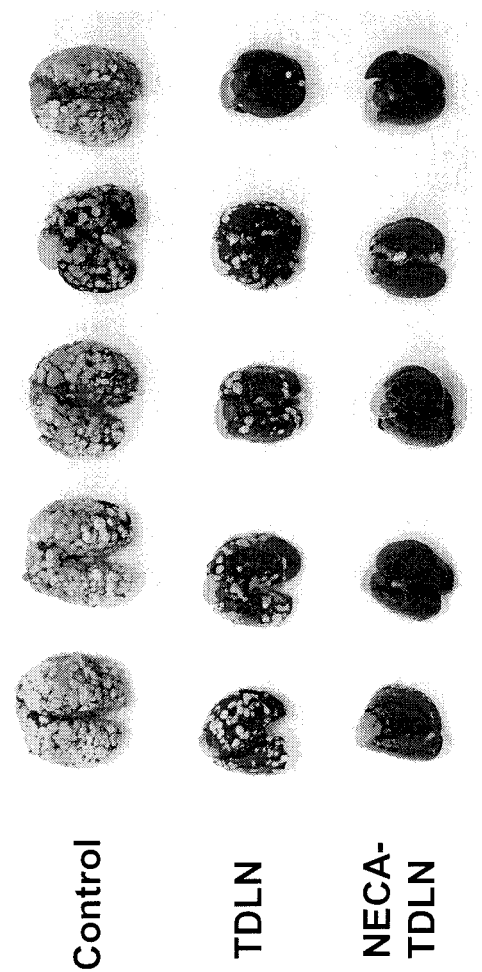

In the first experiment, the anti-tumor effect of NECA-TDLN was compared with normal TDLN. NECA pretreatment of anti-tumor T cells enhanced tumor rejection in vivo (FIG. 1). The number of tumor nodules decreased from 118±51 (TDLN) to 21±33 (NECA-TDLN). The difference was statistically significant (p=0.00045; Student's t-test).

Figure 2:
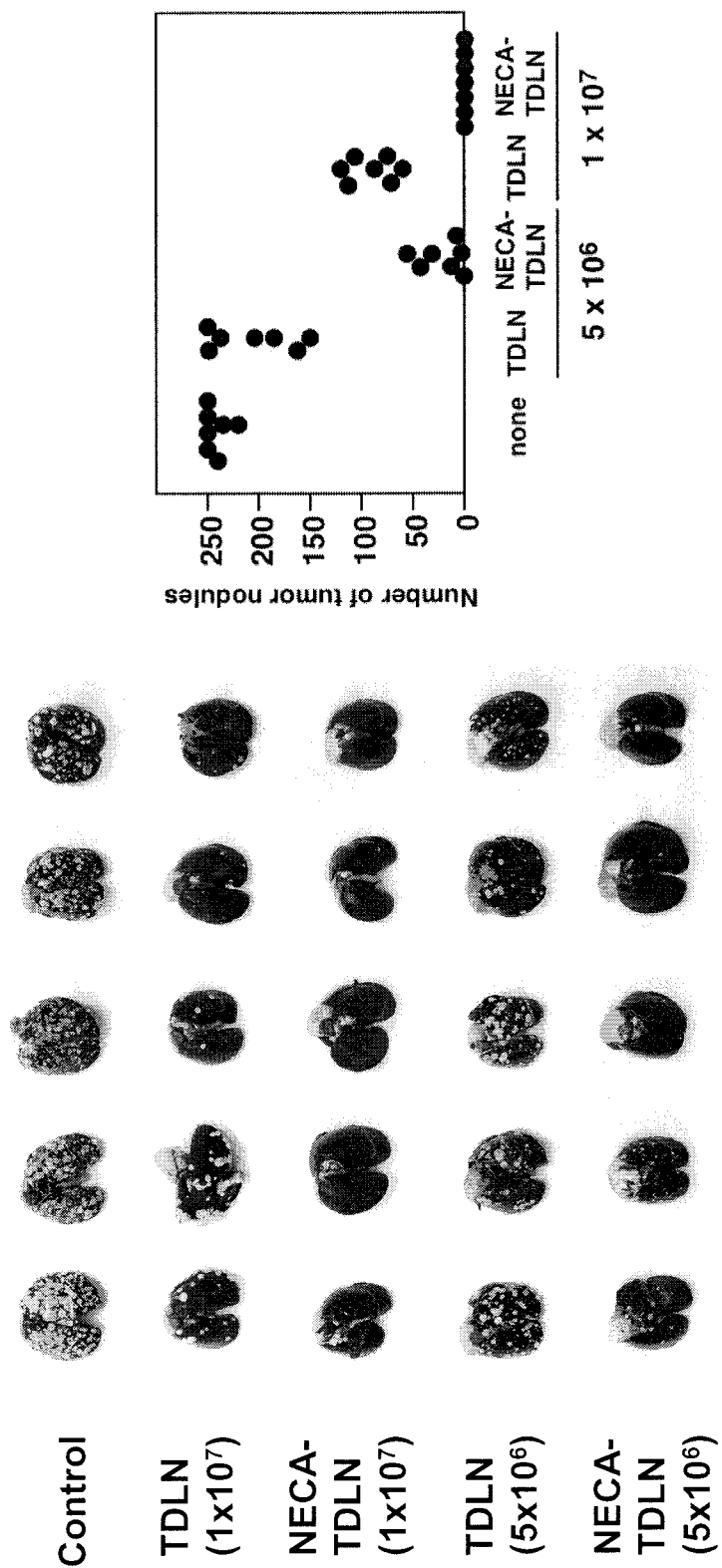

The rejection of tumors by adoptive immunotherapy is dependent on the number of anti-tumor T cells. When $5\times10^6$ cells were injected, TDLN moderately reduced the number of tumor nodules (average=206), while the number of nodules was 22 (average) by the same number of NECA-TDLN (FIG. 2). In this second experiment, there was no visible tumor nodule after the transfer of $1\times10^7$ NECA-TDLN. In parallel, it was confirmed that NECA-TDLN used for the in vivo studies are less sensitive to A2AR-mediated immunosuppression by cytokine assay (data not shown). These results suggest the improvement of adoptive immunotherapy by preincubation of anti-tumor T cells with NECA.

7.2 Example 2

The increased levels of extracellular adenosine in inflamed tissues down-regulate activated immune cells via A2A adenosine receptor. This A2A adenosine receptor-mediated immunosuppression is a disqualifying obstacle in cancer immunotherapy since it protects cancerous tissues from adoptively transferred anti-tumor T cells. The aim of this study was to test whether the negative selection of T cells will produce T cells that are resistant to inhibition by extracellular adenosine.

Experimental Approach:

Cytotoxic T lymphocytes (CTL) were developed by mixed lymphocyte culture in the presence or absence of adenosine receptor agonist 5'-N-ethylcarboxamidoadenosine (NECA). The sensitivity of CTL to adenosine analogs was characterized by cAMP induction, interferon-γ production and cytotoxicity.

Key Results:

CTL which could proliferate even in the presence of NECA were less susceptible to inhibition by A2A adenosine receptor agonists as shown by much smaller cAMP accumulation and less inhibition of interferon-γ production than in control CTL. The successful protocol to produce CTL that are both resistant to adenosine-mediated immunosuppression and maintain strong cytotoxicity and interferon-γ secretion required NECA to be added only during expansion stage after the establishment of CTL. In contrast, the priming of resting T cells in the presence of NECA resulted in T cells with impaired effector functions.

Conclusion and Implications:

Adenosine-resistant effector T cells were successfully obtained by exposure of activated T cells to NECA. These in vitro studies formed the basis to produce anti-tumor T cells that are more effective in adoptive immunotherapy.

Introduction

A2A adenosine receptor is highly expressed in the brain and immune cells (Fredholm et al., 2001; Linden, 2001). Binding of ligands to A2A adenosine receptor expressed on T cells strongly inhibits proliferation (Huang et al., 1997), cytotoxicity (Koshiba et al., 1997), and cytokines production (Koshiba et al., 1997; Lappas et al., 2005; Erdmann et al., 2005). A2B adenosine receptors are also expressed in macrophages, mast cells, and activated T cells (Fredholm et al., 2001; Linden, 2001; Ohta et al., 2006). Since both A2A and A2B adenosine receptor are Gas-coupled receptors, subsequent increase of intracellular cAMP by adenylate cyclase activates PKA (Fredholm et al., 2001; Linden, 2001). Phosphorylation by PKA of COOH-terminal Src kinase (Csk) results in the inhibition of Lck activation and interruption of T cell receptor signaling (Vang et al., 2001). It is also reported that regulatory subunit of PKA plays a role in the inhibition of effector functions of activated T cells (Raskovalova et al., 2007). T cells are expressing other immunosuppressive Gas protein-coupled receptors (i.e. $\beta_2$-adrenoceptor, histamine $H_2$ receptor, prostaglandin $E_2$ ($PGE_2$) receptor); however, A2A adenosine receptor was found to be non-redundant in the mechanism of physiological down-regulation of inflammatory responses (Ohta and Sitkovsky, 2001; Sitkovsky et al., 2004; Sitkovsky and Ohta, 2005; Ohta et al., 2007). Indeed, deficiency of A2A adenosine receptor was demonstrated to exacerbate inflammatory tissue damage (Ohta and Sitkovsky, 2001; Day et al., 2004). A2B adenosine receptor-deficient mice were also reported to have low levels of inflammation in the vascular endothelium (Yang et al., 2006). Thus, A2A/A2B adenosine receptors play an important role in the down-regulation of immune responses.

Tumors may be using the adenosine-mediated immunosuppression to evade the attack of anti-tumor T cells. Because of aggressive growth of tumor cells and tumor geometry, cancerous tissues are often hypoxic. Chronic hypoxia in tumors is known to correlate with poor prognosis (Harris, 2002; Shannon et al., 2003; Vaupel and Mayer, 2007). Because of hypoxia inside tumors, extracellular fluid in tumor tissues maintains higher levels of adenosine than normal tissues (Ohta et al., 2006). Tissue hypoxia is conducive to accumulation of extracellular adenosine because of the inhibition of adenosine kinase (Decking et al., 1997; Kobayashi et al., 2000) and hypoxia-induced upregulation of extracellular adenosine—generating enzymes CD39 and CD73 (Eltzschig et al., 2004; Kobie et al., 2006; Deaglio et al., 2007).

Much enhanced tumor destruction in A2A adenosine receptor-deficient mice demonstrated the role of intratumoral adenosine as a self-protective mechanism of tumors by immunosuppression through A2A adenosine receptor (Ohta et al., 2006). In agreement with such interpretation, antagonists of A2A adenosine receptor significantly improved tumor immunotherapy by T cell adoptive transfer (Ohta et al., 2006). These observations suggest the novel approach whereby more effective immunotherapy will be accomplished by preventing downregulation of adoptively transferred T cell functions via A2A/A2B adenosine receptor. Accordingly, treatments that down-regulate A2A and A2B adenosine receptors in effector T cells are expected to improve adoptive immunotherapy.

This Example describes a study that offers the approach to select CTL which are insensitive to A2A/A2B adenosine receptor-mediated immunosuppression. This may be done by culturing them with 5'-N-ethylcarboxamidoadenosine (NECA) which is an adenosine receptor agonist having high affinity to both A2A and A2B adenosine receptors ($K^d$=10-20 nM) (Fredholm et al., 2001). NECA was shown to lead to suppressed CTL expansion in vitro; however, significant number of cells could still expand even in the presence of high concentration of NECA. These negatively selected CTL were found not to respond to A2A/A2B adenosine receptor stimulation by cAMP accumulation and their effector functions were resistant to extracellular adenosine and A2A/A2B adenosine receptor-mediated immunosuppression.

(1) Methods (a) Mice

C57BL/6 and DBA/2 mice were obtained from Charles River Laboratories (Wilmington, Mass.). The mice were housed in the animal facility of Northeastern University, and were used at 7-9 weeks of age in accordance with institutional animal care guidelines.

(b) Mixed Lymphocyte Culture

Antigen-specific cytotoxic T cells were induced by allogenic mixed lymphocyte culture using spleen cells from C57BL/6 (H-$2^b$) and DBA/2 (H-$2^d$) mice. Spleen cells from DBA/2 mice were pretreated with 50 μg ml$^{-1}$ mitomycin C (Sigma; St. Louis, Mo.) for 30 min at 37° C. After washing three times by centrifugation, $2 \times 10^6$ DBA/2 spleen cells (stimulator) were mixed with $6 \times 10^6$ C57BL/6 spleen cells (responder) in 2 ml of RPMI1640 medium containing 10% fetal calf serum. The cells were cultured for 5 days in a 12 well plastic plate. In some experiments, CTL ($2 \times 10^6$ cells) were restimulated on day 5 using mitomycin C-treated DBA/2 spleen cells ($4 \times 10^6$ cells). The restimulated cells were cultured for additional 2 days, and were analyzed on day 7. NECA (Sigma; St. Louis, Mo.) was added either at the beginning of mixed lymphocyte culture (0-120 h) or after restimulation (120-168 h).

(c) Cytokine Production and Cell Proliferation in Mixed Lymphocyte Culture

Culture supernatant was collected 5 days after the set up of mixed lymphocyte culture or 2 days after restimulation and was stored at 4° C. for subsequent measurement of interferon-γ (IFN-γ) levels. IFN-γ was quantified by ELISA (R&D Systems; Minneapolis, Minn.) according to manufacturer's instruction. Cells were incubated for additional 4 h in the presence of 1 μCi [3H] thymidine (American Radiolabeled Chemicals, St. Louis, Mo.) and radioactivity of incorporated thymidine was counted.

(d) Cytotoxicity Assay

Cytotoxicity of T cells against P815 mastocytoma (H-$2^d$) was determined by $^{51}$Cr release assay. Initially, P815 cells ($2 \times 10^6$) were incubated with 100 μCi [$^{51}$Cr] sodium chromate (Perkin Elmer, Boston, Mass.) for 1 h at 37° C. The cells were washed for three times by centrifugation to remove excess radioactivity. The labeled P815 cells ($1 \times 10^4$ cells) were mixed with the effector cells recovered from mixed lymphocyte culture in a volume of 150 μl. Effector-target ratio was between 5:1 and 1.25:1. Sedimentation of the cells in a v-bottom 96 well plate by brief centrifugation was followed by incubation at 37° C. After 4 h, $^{51}$Cr release in the supernatant from target cells was counted using γ-radiation counter. Spontaneous $^{51}$Cr release was measured by culturing target cells alone. Maximum $^{51}$Cr release was measured by adding 1N hydrochloric acid to the same number of target cells. Cytotoxicity was calculated as percentage cell lysis when spontaneous and maximum $^{51}$Cr release were set to 0% and 100%, respectively.

(e) cAMP Assay

Stimulation of cAMP production and measurement of cAMP levels were performed as described previously (Apasov et al., 2000). After washing twice with media to remove excess NECA, cAMP production from cells ($2 \times 10^5$) were induced by NECA, CGS21680 (A2A adenosine receptor-specific agonist; from Tocris, Ellisville, Mo.), or forskolin (adenylate cyclase activator; from Sigma). The concentration of cAMP inducers were 5 μM. The cells were incubated for 15 min at 37° C., and the reaction was stopped by addition of 1N hydrochloric acid. cAMP levels were determined by ELISA (Amersham Biosciences, Buckinghamshire, UK).

(f) Stimulation of IFN-γ Production from CTL

CTL ($2\times10^5$ cells) were washed twice with media and restimulated by plate-bound anti-CD3 and anti-CD28 monoclonal antibodies (mAb) (BD Biosciences, San Diego, Calif.). Anti-CD3 mAb (2 μg ml$^{-1}$) and anti-CD28 mAb (1 μg ml$^{-1}$) diluted in PBS were immobilized in a flat-bottom 96-well plastic culture plate for 1 h at 37° C. before use. In order to examine anti-tumor cellular response, CTL ($2\times10^5$ cells) were also cultured with mitomycin C-treated P815 mastocytoma ($2.5\times10^5$ cells). Restimulation was performed in the presence of NECA, CGS21680 or forskolin (10 μM) in order to examine sensitivity of T cells to cAMP inducers. Culture supernatant after 24-48 h was assayed for IFN-γ levels by ELISA.

(g) Flowcytometric Analysis

Cells recovered from mixed lymphocyte culture were labeled with phycoerythrin-conjugated anti-CD8, allophycocyanin-conjugated anti-CD4 and fluorescein-conjugated anti-CD69 mAb, and were analyzed by FACSCalibur (BD Biosciences). Cytokine production from CTL was analyzed by intracellular staining as described (Nishimura et al., 1999). After the stimulation with immobilized anti-CD3 and anti-CD28 mAb for 24 h, cells were further incubated in the presence of brefeldin A (10 μg ml$^{-1}$) for 2 h. Cells were fixed with 4% parafolmaldehyde-PBS for 15 min, permeabilized with permeabilizing buffer (50 mM NaCl, 5 mM EDTA, 0.02% $NaN_3$, 0.5% Triton X-100, 10 mM Tris-HCl, pH 7.5) for 15 min, and stained with fluorescein-labeled anti-IFN-γ mAb. IFN-γ-producing CD8$^+$ cells were identified by cell surface staining using phycoerythrin-conjugated anti-CD8 mAb. All antibodies were obtained from BD Biosciences.

For cell proliferation assay, spleen cells from C57BL/6 mouse were labeled with carboxyfluorescein succinimidyl ester (CFSE; Molecular Probes) at 1 μM for 8 min. Excess CFSE was removed by dilution with fetal calf serum and subsequent centrifugation. This washing step was repeated twice. The resulted CFSE-labeled cells were used as a responder in mixed lymphocyte culture. After 3 days, the cells were stained with phycoerythrin-conjugated anti-CD8 mAb, and cell division was analyzed by flowcytometer as indicated by the stepwise decrease of fluorescence intensity of CFSE.

(2) Statistics (3) Data represent mean±SD. Statistical calculations were performed using Student's t-test. Statistical significance was accepted for p values less than 0.05.

(4) Results

Development and Expansion of CTL in the Presence of Adenosine Receptor Agonist NECA In order to examine the effect of NECA on the development of CTL, we started mixed lymphocyte culture with or without NECA using spleen cells from C57BL/6 mice (H-2$^b$) as responders and those from DBA/2 mice (H-2$^d$) as stimulators. After 5 days, NECA, as expected, significantly impaired CTL development in a concentration-dependent manner. Cell proliferation as indicated by [$^3$H] thymidine incorporation decreased to 30-40% in the presence of NECA (FIG. 5A). Correspondingly, there was a decrease in cell numbers in a concentration-dependent manner. The cell number in NECA-treated culture decreased to 78% (0.1 μM), 72% (1 μM) and 68% (10 μM) of control. IFN-γ levels in the culture supernatant decreased to 44% by 10$^{-7}$ M NECA and it was only 18% when incubated with 10$^{-5}$ M NECA (FIG. 5B). Cytotoxicity was also reduced to 33% of control when incubated with 10$^{-5}$ M NECA (FIG. 5C). Interestingly, although a large part of CTL development was impaired, there was a significant number of arising clusters of proliferating cells even at the highest concentration of NECA. Flow cytometric analysis of the cells revealed the expansion of activated T cells in the presence of NECA. The majority of the expanded cells was CD8$^+$ T cells and there were also smaller number of CD4$^+$ T cells. Such profile was similar to CTL developed without NECA (FIG. 5D). Furthermore, significant proliferation of CD8$^+$ cells in the presence of NECA was demonstrated in mixed lymphocyte culture after labeling with CFSE. Note that although the number of activated cells was decreasing dependent on the concentration of NECA, the NECA-treated culture still contains progressively proliferated CD8$^+$ cells as can be seen in the control culture (FIG. 5E). These results suggest that while NECA does strongly suppress T cell activation, some of the CTL can be still activated and expanded even in the presence of NECA.

Selection of Adenosine-Resistant CTL with NECA Present Throughout the Induction

We speculated that the CTL developed in the presence of NECA (named NECA-CTL) could survive because they were less sensitive to signaling by NECA via $A_2$ adenosine receptors. If it is the case, then NECA-CTL may not respond to A2A/A2B adenosine receptor stimulation as much as CTL developed in the absence of NECA (control CTL). In order to test this, we measured cAMP responses of different preparations of CTL to a non-selective A2A/A2B adenosine receptor agonist NECA and A2A adenosine receptor-selective agonist CGS21680 (CGS). Control CTL increased cAMP levels 7.4-fold and 11.1-fold in response to CGS and NECA, respectively (FIG. 6). In contrast, the increase of cAMP levels in NECA-CTL was only 1.3 to 2.4-fold by CGS and 2.2 to 3.1-fold by NECA. The basal cAMP levels were not different in these CTL. Direct activation of adenylate cyclase by forskolin induced high levels of cAMP in both control CTL and NECA-CTL thereby providing an important internal control that it is indeed a difference in $A_2$ adenosine receptors but not intracellular cAMP-producing machinery that explain the differential susceptibility of NECA-CTL vs control CTL to effects of adenosine receptor agonists (FIG. 6). This result indicates that NECA-CTL produced much smaller amount of cAMP than control CTL in response to A2A/A2B adenosine receptor agonists, even though their cAMP-synthesizing mechanism was intact.

The greatly diminished cAMP response of NECA-CTL to adenosine receptor agonists suggested that they would also be more resistant to adenosine-mediated immunosupression. To test this, we stimulated NECA-CTL and control CTL and compared cytokine-producing activities in the presence of A2A/A2B adenosine receptor agonists. It is shown in Table 1 that negatively selected NECA-CTL retained up to 80% of their IFN-γ producing capacity when tested for susceptibility to inhibition by CGS. In contrast, non-selected control CTL retained only 44% of their IFN-γ producing capacity even though absolute amounts of IFN-γ have been higher in control CTL; the maximum IFN-γ producing activity of NECA-CTL was decreased compared with control CTL and this was dependent on the concentration of NECA used to induce NECA-CTL. Control CTL produced 9188 pg ml$^{-1}$ IFN-γ, but the activities in NECA-CTL decreased to 3722 (0.1 μM), 2327 (1 μM) and 1089 (10 μM) pg ml$^{-1}$ (Table 1). Forskolin strongly suppressed IFN-γ production from both control CTL and NECA-CTL (data not shown).

TABLE 1

CTL developed with NECA were resistant to immunosuppression
by A2A/A2B adenosine receptor agonists

| | IFN-γ levels (%) | | |
|---|---|---|---|
| | None | CGS | NECA |
| Control | 100 ± 8 (9188) | 44 ± 11 | 28 ± 7 |
| NECA (0.1 mM) | 100 ± 23 (3722) | 57 ± 8** | 44 ± 12*** |
| NECA (1 mM) | 100 ± 19 (2327) | 67 ± 10* | 56 ± 8*** |
| NECA (10 mM) | 100 ± 5 (1089) | 80 ± 13** | 60 ± 8*** |

CTL induced as described in FIG. 5 were stimulated with immobilized anti-CD3 and anti CD28 mAbs for 24 h in the presence or absence of CGS or NECA (10 mM). Numbers in parentheses are IFN-g levels (pg ml-1). The data represent the IFN-g levels expressed as a % of those in corresponding CTL without CGS/NECA. The statistical significance was calculated by Student's t-test: *P<0.05; P<0.01; *P<0.001 versus control CTL. CGS, CGS21680; CTL, cytotoxic T lymphocytes; IFN-g, interferon-g; NECA, 5'-N-ethylcarboxamidoadenosine.

We interpreted these results to mean that T cell activation and expansion in the presence of NECA led to the selection of CTL which are resistant to the immunosuppressive mechanism via A2A/A2B adenosine receptors. A disadvantage with the induction of NECA-CTL in this way is the impaired effector function of these cells, as shown by diminished cytotoxicity (FIG. 5C) and IFN-γ producibility (Table 1) of the resulting CTL. As NECA was present during the ongoing CTL priming process, it might have interrupted T cell activation and hampered appearance of fully functional CTL. To avoid this drawback, we performed the experiments described below.

Selection of Adenosine-Resistant CTL with NECA Treatment after the Development of CTL In order to produce NECA-CTL which retain comparable effector functions, we initially withheld NECA for 5 days to induce fully functional CTL, and restimulated these CTL with the same stimulator (DBA/2 cells) in the presence or absence of NECA. After the restimulation, NECA again was shown to inhibit proliferation of CTL (FIG. 7A) and IFN-γ levels in the culture supernatant (FIG. 7B). However, contrary to primary mixed lymphocyte culture (FIG. 5), the cytotoxicity was not impaired by NECA treatment (FIG. 7C). In addition, flowcytometric analysis revealed the proportion of CD8$^+$ T cells in the expanded cells was unchanged from control CTL (FIG. 7D). These CTL were restimulated with anti-CD3 mAb to compare IFN-γ producibility. NECA-CTL was found to produce IFN-γ at high levels comparable to control CTL (FIG. 8A). Furthermore, the frequency of IFN-γ producing CD8$^+$ T cells was at the same levels (approximately 60%) in both control and NECA-CTL (FIG. 8B). When added to pre-activated T cells, NECA may suppress the proliferation, but the resulted cells retain equivalent effector activities as control CTL.

The NECA-CTL which was cultured with NECA only after the CTL development were then tested for their susceptibility to A2A/A2B adenosine receptor agonists. When control CTL was restimulated with anti-CD3 mAb, NECA and CGS strongly inhibited IFN-γ production from these cells, whereas NECA-CTL was resistant to the suppressive effect (FIG. 8A). The IFN-γ production in the presence of A2A/A2B adenosine receptor agonists was significantly higher in NECA-CTL than in control CTL (FIG. 8A). It was also the case in the frequency of IFN-γ producing CD8$^+$ T cells. CGS and NECA strongly reduced IFN-γ producers in control CTL by 70% (decreased from 60 to 17-21%), but the reduction in NECA-CTL was only 20-35% (decreased to 36-46%; FIG. 8B). In accordance with the cytokine data, cAMP assay demonstrated the deficiency of NECA-CTL to respond to A2A/A2B adenosine receptor agonists. In contrast to high levels of cAMP response in control CTL, NECA-CTL produced significantly less amount of cAMP when incubated with CGS and NECA (FIG. 8C). Next, NECA-CTL were tested how long they maintain the resistance to adenosine. When IFN-γ production was induced 24 h after removal of NECA, the resistance to A2A adenosine receptor agonist persisted in NECA-CTL induced by 1 or 10 μM NECA (FIG. 9). However, the sensitivity to A2A adenosine receptor stimulation was resumed after 48 h. These results show that the culturing with NECA could induce adenosine-resistant CTL and those CTL that have been exposed to NECA only after the CTL induction could maintain strong effector functions. Although the resistance to adenosine was not permanent, NECA-CTL remained resistant at least for 24 h after the removal of NECA.

We further examined antigen-specific anti-tumor responses of the CTL by culturing with P815 tumor cells. The CTL produced IFN-γ upon recognition of the tumor cells, and the amount of IFN-γ was almost equivalent in control and NECA-CTL (FIG. 10). It was again confirmed that NECA-CTL could produce significantly higher levels of IFN-γ than control CTL when they encountered tumor cells in the presence of A2A/A2B adenosine receptor agonists. Together with the strong cytotoxicity against the tumor cells (FIG. 7C), our results suggest that NECA-CTL may act more effectively than control CTL in adenosine-rich microenvironment.

Discussion and Conclusions

Adoptive transfer of anti-tumor CTL is a promising approach toward tumor eradication (Dudley and Rosenberg, 2003; Gattinoni et al., 2006; Gajewski et al., 2006). CTL may be collected from tumor-bearing host, expanded in vitro, and a large number of anti-tumor effector cells may be returned to the host. However, in spite of their strong anti-tumor activities in vitro, the outcome of previous adoptive immunotherapy techniques has not been satisfactory. Even after successful expansion of anti-tumor effector T cells, anti-tumor responses of adoptively transferred T cells may be disabled in tumor microenvironment. The immunosuppressive mechanisms in tumors include secretion of anti-inflammatory cytokines, i.e. IL-10 (Steinbrink et al., 1999) and TGF-β (Gorelik and Flavell, 2001), induction of T cell apoptosis by programmed death ligand-1 (Iwai et al., 2002), nutrient deficiency by glucose deprivation (Cham and Gajewski, 2005), L-arginine metabolism by myeloid suppressor cells (Rodriguez et al., 2004), and the expression of indoleamine-2,3-dioxygenase (Uyttenhove et al., 2003; Puccetti and Grohmann, 2007). Regulatory T cells may also play a major role in the suppression of T cell activation in tumors (Sutmuller et al., 2001; Turk et al., 2004; Curiel et al., 2004; Antony et al., 2005). It is known that lymphodepletion before adoptive transfer improves T cell responses (Cheever et al., 1980; Gattinoni et al., 2006). This effect at least in part can be explained by the depletion of regulatory T cells. Regulatory T cells produce anti-inflammatory molecules such as IL-10 (Asseman et al., 1999; Annacker et al., 2001; von Boehmer, 2005), TGF-β (Powrie et al., 1996; Chen et al., 2005; von Boehmer, 2005) and galectin-1 (Garín et al., 2007; Rabinovich et al., 2007). If anti-tumor effectors resistant to such immunosuppressive mechanisms are available, those cells may improve the outcome of tumor immunotherapy.

Recently, we found that extracellular adenosine in hypoxic tumor microenvironment represents a non-redundant and powerful defensive mechanism that protects tumors from anti-tumor T cells (Ohta et al., 2006). Although tissue hypoxia leads to accumulation of extracellular adenosine, regulatory T cells may also be a potential source of adenosine, because they were found to express CD39 and CD73 (Kobie et al., 2006; Deaglio et al., 2007), which catalyze degradation of ATP/AMP to adenosine. We demonstrated in experiments using A2A adenosine receptor-deficient mice that the efficacy of anti-tumor T cells is restricted in adenosine-rich tumor microenvironment (Ohta et al., 2006). When adoptive immunotherapy was combined with adenosine receptor antagonists including caffeine, there was significant improvement in the inhibition of lung metastasis and growth retardation of subcutaneous tumors (Ohta et al., 2006). This previous study prompted us to establish anti-tumor T cells which lack functional A2A/A2B adenosine receptor.

In our present study, CTL development was strongly, but not completely, impaired in the presence of NECA (FIG. 5). Significant number of T cells could manage to survive this hostile environment, and the survived cells were insensitive to A2A/A2B adenosine receptor agonists. Importantly, A2A and A2B adenosine receptors are known to down-modulate upon treatment with agonists. This regulation involves desensitization by G protein-coupled receptor kinases and internalization of the receptors (Klaasse et al., 2008; Zezula and Freissmuth, 2008). After the culture with NECA, CTL might become insensitive to adenosine because of temporal down-modulation of the receptors. This explanation corresponds well with the result in FIG. 10 showing resumption of the sensitivity to A2A adenosine receptor agonist after 48 h.

Another possible explanation for the proliferation of CTL despite the presence of NECA is that A2A/A2B adenosine receptor expression in CD8+ T cells might be heterogeneous. T cells in general are known to express relatively high levels of A2A adenosine receptor (Fredholm et al., 2001; Linden, 2001), but the distribution of these receptors within T cell subsets are not known. The lack of adequate antibodies against A2A and A2B adenosine receptor is restricting identification of heterogeneous expression of these receptors. If there are T cell subpopulations expressing different levels of A2A/A2B adenosine receptors, certain fraction of CD8+ T cells may respond at only low levels to A2A/A2B adenosine receptor, while many of the CD8+ T cells are high responders. Activation of A2A/A2B adenosine receptor-high CD8+ T cells will be strongly suppressed by NECA, but not A2A/A2B adenosine receptor-low population, resulting in the selective proliferation of adenosine-resistant CD8+ T cells. This hypothesis is consistent with the early proliferation of NECA-CTL (FIG. 5E) and their marginal response to A2A/A2B adenosine receptor agonists (FIG. 6 and Table 1).

This adenosine-resistant CTL is expected to be more effective in tumor microenvironment; however, CTL developed in the presence of NECA suffered from their impaired anti-tumor effector activities as shown by the strong reduction of cytotoxicity (FIG. 5) and IFN-γ producibility (Table 1). Such CTL may not be efficient enough to destroy the tumor in vivo even though they are insensitive to adenosine. The interruption by NECA of T cell full activation in the priming stage might have caused the expansion of CTL with poor effector functions. Our results in FIG. 5 and Table 1 are consistent with a recent publication showing the induction of "anergic" T cells in the presence of A2A adenosine receptor agonist (Zarek et al., 2008). While the precise mechanism of these poor effector functions is not clear, FIG. 6 suggests changes in cAMP content of the cells are not responsible for the incomplete expression of the effector functions in NECA-CTL.

Although immunosuppressive effects of A2A adenosine receptor agonists have been demonstrated using resting T cells (Huang et al., 1997; Lappas et al., 2005; Sevigny et al., 2007; Zarek et al., 2008), it was originally not clear whether the addition of NECA subsequent to establishment of activated CTL, in which strong cytotoxicity and IFN-γ producibilities were already induced, can down-regulate these effector functions. We restimulated control CTL in the presence of NECA and found that proliferative responses were still attenuated by NECA (FIG. 7A). IFN-γ levels in the supernatant were also decreased (FIG. 7B) corresponding to the inhibition of proliferation. This partial inhibition of restimulated T cells may reflect the presence of high responders to A2A/A2B adenosine receptor agonists in the established control CTL. The restimulated cells which survived NECA treatment were again shown to be resistant to A2A/A2B adenosine receptor agonists (FIGS. 8, 10). Furthermore, in this treatment protocol, the resulting NECA-CTL retained equivalent cytotoxicity (FIG. 7C) and comparable IFN-γ producing activity to control-CTL (FIGS. 8, 10). Therefore, the problem in NECA-CTL, i.e. diminished effector functions, could be overcome by withholding NECA during development of CTL.

A2A adenosine receptor is upregulated upon T cell activation and negatively regulates proinflammatory cytokines (Koshiba et al., 1999; Lappas et al., 2005). Although NECA is immunosuppressive to both resting (primary mixed lymphocyte culture) and activated T cells (restimulated CTL), the effector functions of activated T cells are relatively resistant to NECA comparing to resting T cells (FIG. 5C vs FIG. 7C and Table 1 vs FIG. 8A). This result is in accordance with a study showing no CGS21680-mediated inhibition of cytotoxicity and only minor decrease of IFN-γ production from activated CD8+ T cells (Erdmann et al., 2005). Activated T cells are less responsive than resting T cells to negative stimulation from PGE$_2$ receptors and β$_2$-adrenoceptors, both of which are coupled with Gs protein and induce cAMP (Heijink et al., 2003). This difference was correlated with the impairment of phosphorylation of cAMP responsive element binding protein (CREB) in response to PGE$_2$ or β$_2$-agonist (Heijink et al., 2003), suggesting that signaling events downstream of A2A adenosine receptor might be different between resting and activated T cells.

In conclusion, we successfully established antigen-specific CTL, which are partially resistant to adenosine-mediated immunosuppression, after selection using NECA. This CTL retained strong effector functions when NECA treatment started after the development of activated CTL. The use of NECA-CTL for adoptive transfer may be useful to improve immunotherapy.

The study described has been published as a research paper, Ohta et al., British Journal of Pharmacology (2009) 156, 297-306; which contains detailed citations for the references cited above in the Examples and is hereby incorporated by reference in its entirety.

The invention claimed is:

1. A method of making a lymphocyte preparation, comprising:
    (a) collecting an enriched population of tumor-reactive lymphocytes and/or a natural killer cell population from a subject;
    (b) culturing and/or expanding the enriched population of tumor-reactive lymphocytes and/or the natural killer cell population in vitro in the absence of an adenosine receptor agonist; and (c) culturing and/or expanding the enriched population of tumor-reactive lymphocytes and/or the natural killer cell population from (b) in vitro in the presence of an agonist of an adenosine receptor, thereby making a lymphocyte preparation wherein the lymphocyte preparation has anti-tumor activity.

2. The method of claim 1, wherein step (a), (b) or (c) further comprises genetically modifying the enriched population of tumor-reactive lymphocytes and/or a natural killer cell population with a recombinant T cell receptor.

3. The method of claim 1, further comprising enriching the tumor-reactive lymphocytes and/or the natural killer cell population of step (c) for cells resistant to adenosine.

4. The method of claim 1, further comprising removing from the enriched population of tumor-reactive lymphocytes and/or the natural killer cell population of step (c) cells sensitive to inhibition by adenosine.

5. The method of claim 1, further comprising transfecting the enriched population of tumor-reactive lymphocytes and/or the natural killer cell population with a recombinant T cell receptor specific to an antigen.

6. The method of claim 1, further comprising a step of adding an immune cell stimulating ligand to the enriched population of tumor-reactive lymphocytes and/or the natural killer cell population.

7. The method of claim 6, wherein the immune cell stimulating ligand is an anti-CD3 and/or anti-CD28 antibody.

8. The method of claim 1, wherein the subject is human.

9. The method of claim 1, wherein the lymphocyte preparation comprises tumor infiltrating lymphocytes, tumor-reactive lymphocytes, natural killer cells, or lymphokine-activated killer cells.

10. The method of claim 1, further comprising formulating a medicament comprising the lymphocyte preparation.

11. The method of claim 1, wherein the enriched population of tumor-reactive lymphocytes and/or a natural killer cell population is cultured or expanded for about five days in the absence of an adenosine receptor agonist, and then for about two days in the presence of an adenosine receptor agonist.

12. The method of claim 1, wherein the lymphocyte preparation is capable of inhibiting a tumor in vivo.

13. The method of claim 1, wherein the lymphocyte preparation is resistant to inhibition in inflamed or diseased tissues in vivo.

14. A method of making a lymphocyte preparation, comprising:
(a) collecting a cytotoxic T lymphocyte population from a subject;
(b) culturing and/or expanding the cytotoxic T lymphocyte population in vitro in the absence of an adenosine receptor agonist;
(c) culturing and/or expanding the cytotoxic T lymphocyte population from (b) in vitro in the presence of an agonist of an adenosine receptor, and
(d) genetically modifying the cells of either (a), (b) or (c) with a recombinant T cell receptor specific to a tumor antigen, thereby making a lymphocyte preparation wherein the lymphocyte preparation has anti-tumor activity.

15. The method of claim 14, further comprising enriching the cytotoxic T lymphocyte population of step (c) for cells resistant to adenosine.

16. The method of claim 14, further comprising removing from the cytotoxic T lymphocyte population of step (c) cells sensitive to inhibition by adenosine.

17. The method of claim 14, wherein step (d) comprises transfecting the cytotoxic T lymphocyte population with a recombinant T cell receptor specific to an antigen.

18. The method of claim 14, further comprising a step of adding an immune cell stimulating ligand to the cytotoxic T lymphocyte population.

19. The method of claim 18, wherein the immune cell stimulating ligand is an anti-CD3 and/or anti-CD28 antibody.

20. The method of claim 14, wherein the subject is human.

21. The method of claim 14, wherein the lymphocyte preparation comprises cytotoxic T lymphocytes or lymphokine-activated killer cells.

22. The method of claim 14, further comprising formulating a medicament comprising the lymphocyte preparation.

23. The method of claim 14, wherein cytotoxic T lymphocyte population is cultured or expanded for about five days in the absence of an adenosine receptor agonist, and then for about two days in the presence of an adenosine receptor agonist.

24. The method of claim 14, wherein the lymphocyte preparation is capable of inhibiting a tumor in vivo.

25. The method of claim 14, wherein the lymphocyte preparation is resistant to inhibition in inflamed or diseased tissues in vivo.

26. A method of making a lymphocyte preparation, comprising:
(a) collecting a cytotoxic T lymphocyte population from a subject;
(b) culturing and/or expanding said cytotoxic T lymphocyte population in vitro in the absence of an adenosine receptor agonist and under conditions selective for cytotoxic T lymphocytes that recognize tumor cells; and
(c) culturing and/or expanding the tumor cell specific cytotoxic T lymphocyte population from (b) in vitro in the presence of an agonist of an adenosine receptor, thereby making a lymphocyte preparation wherein the lymphocyte preparation has anti-tumor activity.

27. The method of claim 26, further comprising enriching the cytotoxic T lymphocyte population of step (c) for cells resistant to adenosine.

28. The method of claim 26, further comprising removing from the cytotoxic T lymphocyte population cells of step (c) sensitive to inhibition by adenosine.

29. The method of claim 26, further comprising genetically modifying the cytotoxic T lymphocyte population with a recombinant T cell receptor specific to an antigen.

30. The method of claim 26, further comprising tranfecting the cytotoxic T lymphocyte population with a recombinant T cell receptor specific to an antigen.

31. The method of claim 26, further comprising a step of adding an immune cell stimulating ligand to the cytotoxic T lymphocyte population.

32. The method of claim 31, wherein the immune cell stimulating ligand is an anti-CD3 and/or anti-CD28 antibody.

33. The method of claim 26, wherein the subject is human.

34. The method of claim 26, wherein the lymphocyte preparation comprises cytotoxic T lymphocytes or lymphokine-activated killer cells.

35. The method of claim 26, further comprising formulating a medicament comprising the lymphocyte preparation.

36. The method of claim 26, wherein cytotoxic T lymphocyte population is cultured or expanded for about five days in the absence of an adenosine receptor agonist, and then for about two days in the presence of an adenosine receptor agonist.

37. The method of claim 26, wherein the lymphocyte preparation is capable of inhibiting a tumor in vivo.

38. The method of claim 26, wherein the lymphocyte preparation is resistant to inhibition in inflamed or diseased tissues in vivo.

\* \* \* \* \*

UNITED STATES PATENT AND TRADEMARK OFFICE
CERTIFICATE OF CORRECTION

PATENT NO. : 8,883,500 B2
APPLICATION NO. : 13/133121
DATED : November 11, 2014
INVENTOR(S) : Michail V. Sitkovsky and Akio Ohta Page 1 of 1

It is certified that error appears in the above-identified patent and that said Letters Patent is hereby corrected as shown below:

In the Specification

Column 1, Lines 18-21, should read:
--This invention was made with government support under Grant Numbers CA111985, CA112561 and AT002788 awarded by the National Institutes of Health. The government has certain rights in the invention.--

Signed and Sealed this
Twenty-third Day of March, 2021

Drew Hirshfeld
*Performing the Functions and Duties of the*
*Under Secretary of Commerce for Intellectual Property and*
*Director of the United States Patent and Trademark Office*